United States Patent
Nicholas

(10) Patent No.: US 10,253,847 B2
(45) Date of Patent: Apr. 9, 2019

(54) ELECTROMECHANICAL SURGICAL DEVICES WITH SINGLE MOTOR DRIVES AND ADAPTER ASSEMBLIES THERFOR

(71) Applicant: Covidien LP, Mansfield, MA (US)

(72) Inventor: David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 294 days.

(21) Appl. No.: 15/368,869

(22) Filed: Dec. 5, 2016

(65) Prior Publication Data

US 2017/0175852 A1 Jun. 22, 2017

Related U.S. Application Data

(60) Provisional application No. 62/270,804, filed on Dec. 22, 2015.

(51) Int. Cl.
| | |
|---|---|
| *F16H 1/22* | (2006.01) |
| *A61B 17/28* | (2006.01) |
| *A61B 17/072* | (2006.01) |
| *A61B 17/10* | (2006.01) |
| *F16H 25/18* | (2006.01) |
| *A61B 17/00* | (2006.01) |
| *A61B 17/29* | (2006.01) |

(52) U.S. Cl.
CPC ............ *F16H 1/22* (2013.01); *A61B 17/072* (2013.01); *A61B 17/07207* (2013.01); *A61B 17/10* (2013.01); *A61B 17/28* (2013.01); *F16H 25/18* (2013.01); *A61B 2017/00017* (2013.01); *A61B 2017/0046* (2013.01); *A61B 2017/00221* (2013.01); *A61B 2017/00393* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/2927* (2013.01)

(58) Field of Classification Search
CPC .................................. F16H 1/22; A61B 17/28
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Extended European Search Report corresponding to counterpart International Application No. EP 14 18 4882.0 dated May 12, 2015.

(Continued)

*Primary Examiner* — Ha Dinh Ho

(57) ABSTRACT

The present disclosure relates to surgical systems including hand-held electromechanical surgical devices and adapter assemblies for connecting surgical loading units to the hand-held electromechanical surgical devices. The presently described electromechanical surgical devices include single motor drives that selectively drive various output assemblies coordinated by selector motors to operate the surgical loading units.

20 Claims, 23 Drawing Sheets

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |

(56) References Cited

U.S. PATENT DOCUMENTS

| | | |
|---|---|---|
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,763,661 B2* | 9/2017 | Zergiebel ............ H01R 13/405 |
| 10,111,665 B2* | 10/2018 | Aranyi ............ A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |

(56) References Cited

U.S. PATENT DOCUMENTS

| | | |
|---|---|---|
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0166717 A1 | 6/2014 | Swayze et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0118201 A1 | 4/2016 | Nicholas et al. |
| 2016/0310134 A1* | 10/2016 | Contini ............ A61B 17/07207 |
| 2016/0324518 A1* | 11/2016 | Nicholas ............ A61B 17/072 |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |

(56) References Cited

FOREIGN PATENT DOCUMENTS

| | | |
|---|---|---|
| EP | 1769754 A1 | 4/2007 |
| EP | 1813211 A2 | 8/2007 |
| EP | 1982657 A2 | 10/2008 |
| EP | 2055243 A2 | 5/2009 |
| EP | 2316345 A1 | 5/2011 |
| EP | 2668910 A2 | 12/2013 |
| EP | 2792308 A2 | 10/2014 |
| ES | 2333509 A1 | 2/2010 |
| JP | 2005-125075 A | 5/2005 |
| KR | 20120022521 A | 3/2012 |
| WO | 2009/039506 A1 | 3/2009 |
| WO | 2011/108840 A2 | 9/2011 |
| WO | 2012/040984 A1 | 4/2012 |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
Extended European Search Report issued in EP 16205717 dated May 15, 2017.

* cited by examiner

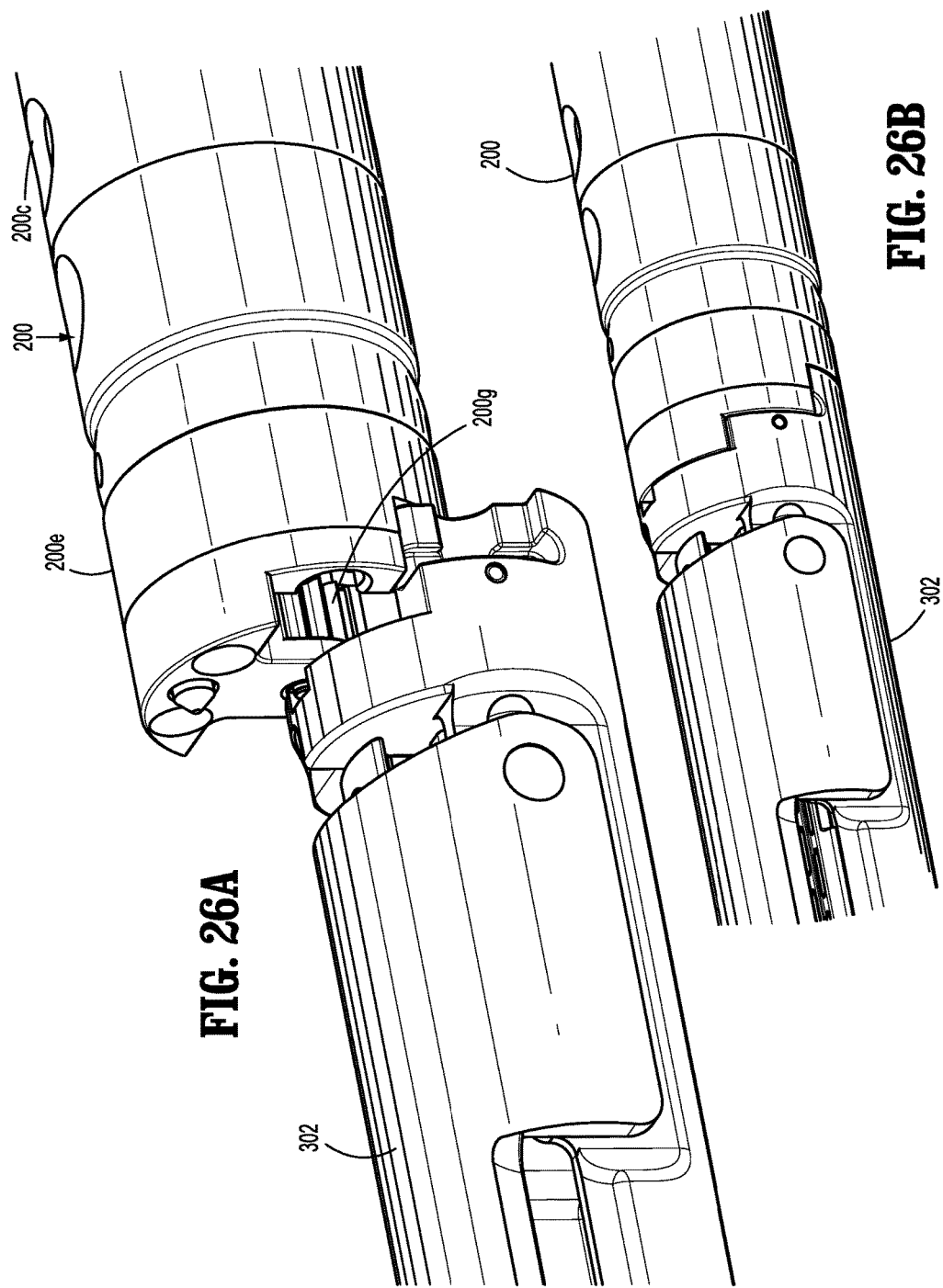

ELECTROMECHANICAL SURGICAL DEVICES WITH SINGLE MOTOR DRIVES AND ADAPTER ASSEMBLIES THERFOR

CROSS-REFERENCE TO RELATED APPLICATIONS

This application claims the benefit of and priority to U.S. Provisional Patent Application No. 62/270,804 filed Dec. 22, 2015, the entire disclosure of which is incorporated by reference herein.

TECHNICAL FIELD

The present disclosure relates to surgical systems, and more specifically, to surgical systems having electromechanical surgical devices, including hand-held electromechanical surgical devices, with single motor drives and adapter assemblies for interconnecting the electromechanical surgical devices to end effectors or surgical loading units.

BACKGROUND

A number of surgical device manufacturers have developed product lines with proprietary powered drive systems for operating and/or manipulating the surgical device. In many instances, the surgical devices include a powered handle assembly, which may be reusable, and an end effector and/or loading unit that is selectively connected to the powered handle assembly prior to use. The powered handle assembly may be disconnected from the loading unit and/or end effector following use so that the end effector, loading unit and/or handle assembly may be disposed of, or in some instances, sterilized for re-use.

Many of the existing end effectors for use with many of the existing powered surgical devices and/or handle assemblies are driven by a linear force. For examples, end effectors or loading units for performing endo-gastrointestinal anastomosis procedures, end-to-end anastomosis procedures and transverse anastomosis procedures, each typically require a linear driving force in order to be operated. Thus, these end effectors or loading units are not compatible with surgical devices and/or handle assemblies that use a rotary motion to deliver power or the like.

In order to make the linear driven end effectors or loading units compatible with powered surgical devices and/or handle assemblies that use a rotary motion to deliver power, adapter assemblies are used to interface between and interconnect the linear driven end effectors with the powered rotary driven surgical devices and/or handle assemblies. Many of these surgical devices and/or adapter assemblies are complex devices including many parts and requiring extensive labor to assemble.

Accordingly, a need exists to develop surgical devices and/or adapter assemblies that incorporate fewer parts, are less labor intensive to assemble, and are ultimately more economical to manufacture and use.

SUMMARY

The present disclosure relates to surgical systems, and more specifically, to surgical systems having electromechanical surgical devices, including hand-held electromechanical surgical devices, with single motor drives and adapter assemblies for interconnecting the electromechanical surgical devices to end effectors or loading units. The electromechanical surgical devices include handle assemblies supporting selector motors that coordinate engagement of output assemblies and the single motor drives. The output assemblies engage input couplers supported by the adapter assemblies. The input couplers can be operatively coupled to the end effectors or loading units so that rotation forces from of the output assemblies enable the end effectors or loading units to perform one or more functions.

According to an aspect of the present disclosure, an electromechanical surgical system includes a handle assembly, a drive motor, a selector cam, a selector motor, a first output assembly, and a second output assembly.

The drive motor may be supported in the handle assembly and may extend to a drive gear.

The selector cam may define a recess. The selector cam may include a compression surface adjacent to the recess of the selector cam. In some embodiments, the recess includes tapered sidewalls.

The selector motor may extend to a selector gear. The selector gear may be positioned to move the selector cam between a first position and a second position.

The first output assembly includes a first output shaft and a first output gear. The first output shaft is selectively coupled to the first output gear by a first engagement key. The first output gear is rotatable with the drive gear of the drive motor. The first engagement key is positionable within the recess of the selector cam while the selector cam is in the first position to engage the first output gear with the first output shaft. The first output shaft is rotatable with the first output gear in response to rotation of the drive gear of the drive motor while the first output gear is coupled to the first output shaft. The first output gear is rotatable relative to the first output shaft while the selector cam is in the second position.

The second output assembly includes a second output shaft and a second output gear. The second output shaft is selectively coupled to the second output gear by a second engagement key. The second output gear is engaged with the first output gear of the first output assembly. The second engagement key is positionable within the recess of the selector cam while the selector cam is in the second position to engage the second output gear with the second output shaft. The second output shaft is rotatable with the second output gear in response to rotation of the drive gear of the drive motor while the second output gear is coupled to the second output shaft. The second output gear is rotatable relative to the second output shaft while the selector cam is in the first position.

In some embodiments, the first engagement key and the first output shaft may be coupled by a first spring. The first spring may be positioned to bias the first engagement key toward the selector cam. The compression surface of the selector cam may be positioned to urge the first engagement key toward the first output shaft and exert compression forces on the first spring while the first engagement key is in contact with the compression surface of the selector cam.

In certain embodiments, the first engagement key may include a flange extending therefrom and the first output gear may include inner teeth. The flange of the first engagement key may be slidable through a slot defined in the first output shaft between a disengaged position and an engaged position to selectively engage the first output gear with the first output shaft. In the engaged position, the flange of the first engagement key may be engaged with the inner teeth of the first output gear and the slot of the first output shaft so that the first output shaft rotates with the first output shaft. In the disengaged position, the flange of the first engagement key may be engaged with the slot of the first output shaft and spaced from the first output gear such that the first output gear rotates relative to the first output shaft.

The first engagement key may include a rounded tip configured to cam along the tapered sidewalls of the recess of the selector cam as the selector cam moves between the first and second positions.

In certain embodiments, the second engagement key and the second output shaft may be coupled by a second spring positioned to bias the second engagement key toward the selector cam. The compression surface of the selector cam may be positioned to urge the second engagement key toward the second output shaft and exert compression forces on the second spring while the second engagement key is in contact with the compression surface of the selector cam.

In some embodiments, the second engagement key may include a flange extending therefrom and the second output gear may include inner teeth. The flange of the second engagement key may be slidable through a slot defined in the second output shaft between a disengaged position and an engaged position to selectively engage the second output gear with the second output shaft. In the engaged position, the flange of the second engagement key may be engaged with the inner teeth of the second output gear and the slot of the second output shaft so that the second output shaft rotates with the second output shaft. In the disengaged position, the flange of the second engagement key may be engaged with the slot of the second output shaft and spaced from the second output gear such that the second output gear rotates relative to the second output shaft.

In certain embodiments, the second engagement key includes a rounded tip configured to cam along the tapered sidewalls of the recess of the selector cam as the selector cam moves between the first and second positions.

The electromechanical surgical system may include a third output assembly including a third output shaft and a third output gear. The third output shaft may be selectively coupled to the third output gear by a third engagement key. The third output gear may be engaged with the first output gear of the first output assembly. The third engagement key may be positionable within the recess of the selector cam while the selector cam is in a third position to engage the third output gear with the third output shaft. The third output shaft may be rotatable with the third output gear in response to rotation of the drive gear of the drive motor while the third output gear is engaged with the third output shaft. The third output gear may be rotatable relative to the third output shaft while the selector cam in is in the first and second positions.

In some embodiments, the third engagement key and the third output shaft may be coupled by a third spring. The third spring may be positioned to bias the third engagement key toward the selector cam.

The compression surface of the selector cam may be positioned to urge the third engagement key toward the third output shaft and exert compression forces on the third spring while the third engagement key is in contact with the compression surface of the selector cam.

In certain embodiments, the third engagement key may include a flange extending therefrom and the third output gear may include inner teeth. The flange of the third engagement key may be slidable through a slot defined in the third output shaft between a disengaged position and an engaged position to selectively engage the third output gear with the third output shaft. In the engaged position, the flange of the third engagement key may be engaged with the inner teeth of the third output gear and the slot of the third output shaft such that the third output gear and the third output shaft move together. In the disengaged position, the flange of the third engagement key may be engaged with the slot of the third output shaft and spaced from the third output gear so that the third output gear rotates relative to the third output shaft.

According to another aspect of the present disclosure, an electromechanical surgical system includes an adapter assembly having proximal and distal ends, an end effector removably coupled to the distal end of the adapter assembly, and a handle assembly coupled to the proximal end of the adapter assembly. The adapter assembly may be removably coupled to the handle assembly by one or both of: a spring loaded button or a spring loaded ejector pin.

The handle assembly includes a drive motor, a drive gear coupled to the drive motor, a selector cam defining a recess, and a selector motor extending to a selector gear. The selector gear may be positioned to move the selector cam between a first position and a second position. The handle assembly further includes a first output assembly and a second output assembly.

The first output assembly includes a first output shaft and a first output gear. The first output gear may be rotatable with the drive gear of the drive motor. The first output shaft may be rotatable with the first output gear while the selector cam is in the first position.

The second output assembly includes a second output shaft and a second output gear. The second output gear may be engaged with the first output gear of the first output assembly. The second output shaft may be rotatable with the second output gear while the selector cam is in the second position.

In some embodiments, one or both of the first and second output shafts is selectively coupled to a respective one of the first and second output gears by an engagement key.

According to yet another aspect of the present disclosure, an electromechanical surgical system includes an adapter assembly, an end effector, and a handle assembly.

The adapter assembly has proximal and distal ends. The proximal end of the adapter assembly may include first and second input couplers. The loading unit may be removably coupled to the distal end of the adapter assembly and operably coupled to the first and second input couplers of the adapter assembly. The handle assembly is coupled to the proximal end of the adapter assembly.

In some embodiments, the handle assembly includes a drive motor, a drive gear coupled to the drive motor, a selector cam defining a recess, and a selector motor extending to a selector gear. The selector gear may be positioned to move the selector cam between a first position and a second position. The handle assembly may include a first output gear rotatable with the drive gear of the drive motor, a first output shaft rotatable with the first output gear and coupled to the first input coupler of the adapter assembly to drive the first input coupler while the selector cam is in the first position, a second output gear engaged with the first output gear, and a second output shaft rotatable with the second output gear and coupled to the second input coupler of the adapter assembly to drive the second input coupler while the selector cam is in the second position.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the disclosure given below, serve to explain the principles of the disclosure, wherein:

FIGS. 26A and 26B are progressive views illustrating the exemplary end effector of FIG. 25 being attached to the electromechanical surgical system of FIG. 1; and

DETAILED DESCRIPTION

Figure 1:
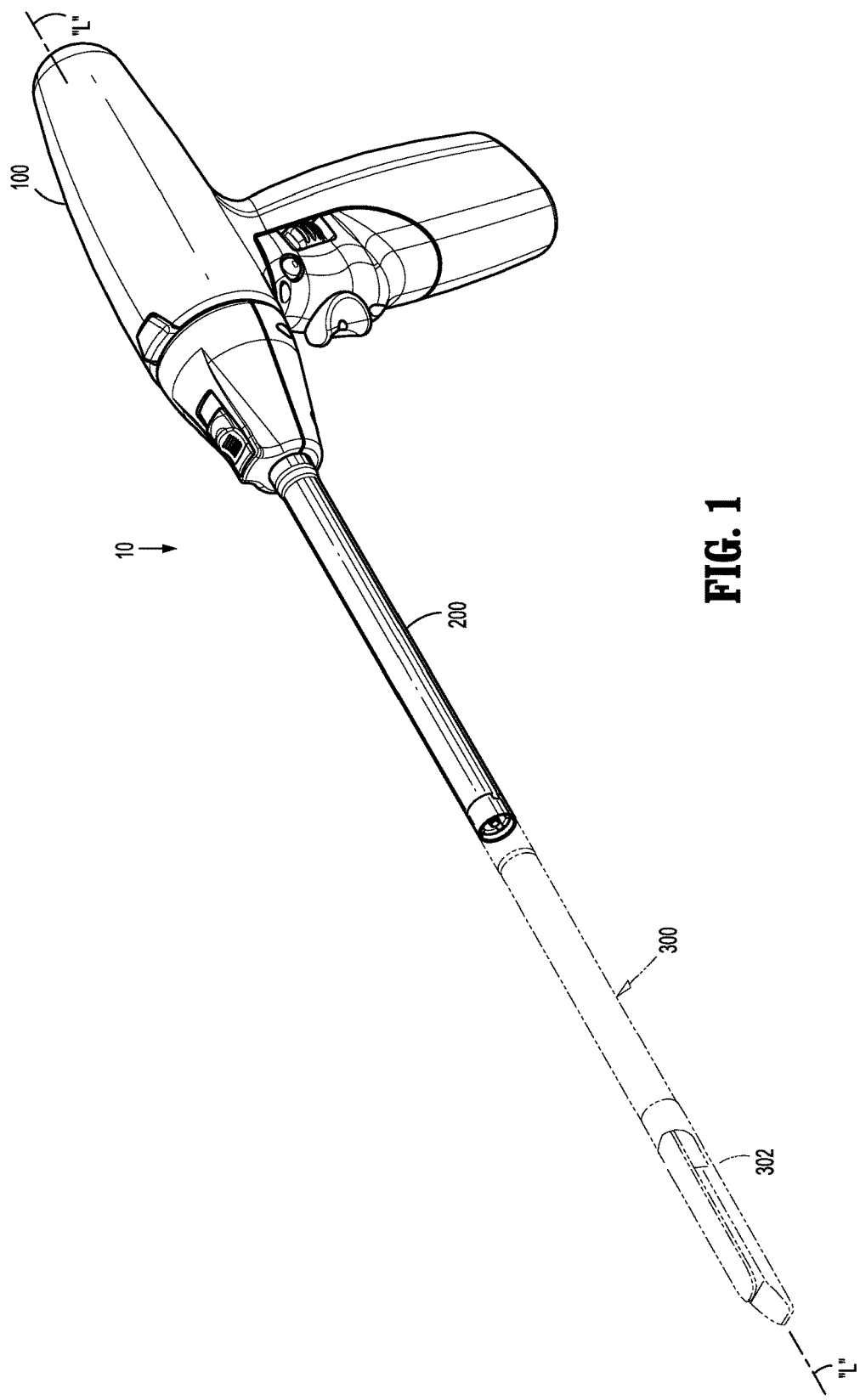
FIG. 1 is a perspective view of an electromechanical surgical system in accordance with the principles of the present disclosure with an exemplary loading unit shown connected thereto in phantom for clarity.

Electromechanical surgical systems of the present disclosure include surgical devices in the form of powered hand-held electromechanical instruments configured for selective attachment to a plurality of different end effectors that are each configured for actuation and manipulation by the powered hand-held electromechanical surgical instrument. In particular, the presently described electromechanical surgical systems include adapter assemblies that interconnect the powered hand-held electromechanical surgical instruments to the plurality of different end effectors for effectuating actuation and/or manipulation thereof.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein, the term "distal" or "leading" refers to that portion of the system, assembly, device, and/or component thereof, farther from the user, while the term "proximal" or "trailing" refers to that portion of the system, assembly, device, and/or component thereof, closer to the user. As used herein, the term "clinician" refers to a doctor, nurse, or other care provider and may include support personnel. As used herein, the term "subject" refers to a human patient or other animal.

Figure 2:
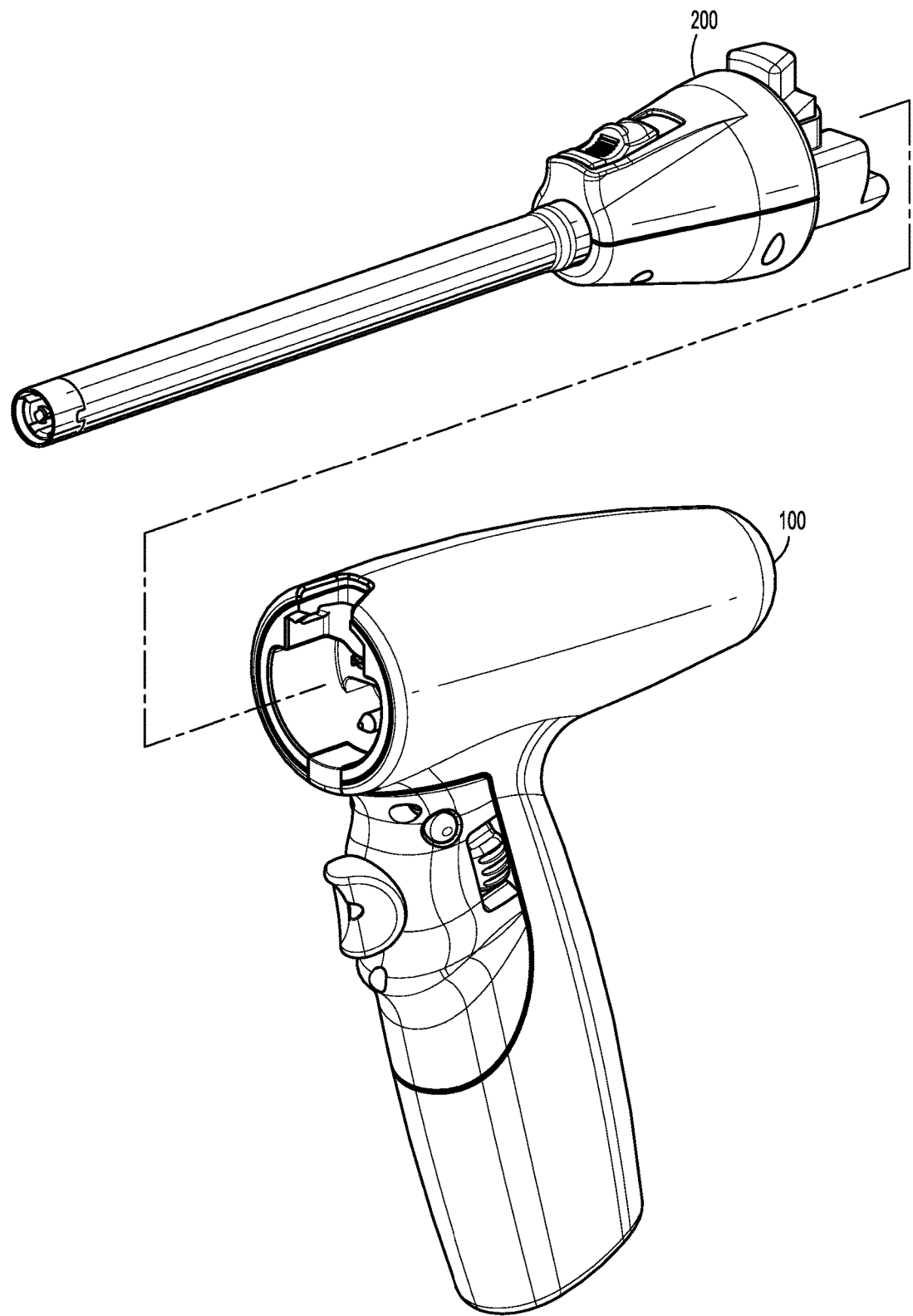
FIG. 2 is a perspective view, with parts separated, of the electromechanical surgical system of FIG. 1.

Turning now to FIGS. 1 and 2, an electromechanical surgical system in accordance with the present disclosure, generally referred to as 10, includes a surgical device or handle assembly 100 in the form of a powered hand-held electromechanical instrument and an adapter assembly 200. Handle assembly 100 is configured for selective connection with adapter assembly 200 and adapter assembly 200 is configured for removable connection to a loading unit 300 (e.g., multiple- or single-use loading unit) including an end effector 302 and/or directly to end effector 302. Together, handle assembly 100 and adapter assembly 200 may cooperate to actuate loading unit 300 and/or end effector 302. Handle assembly 100, adapter assembly 200, and loading unit 300 (and/or end effector 302) define a longitudinal axis "L" therethrough.

In the interest of brevity, although loading unit 300 (and/or end effector 302) is described herein as including surgical stapling components, the loading unit 300 (and/or end effector 302) of the present disclosure may include, or be adapted to include, any type of surgical components. For example, loading unit 300 (and/or end effector 302), or components thereof, may include, but is/are not limited to, one or more components of a surgical stapler, a surgical clip applier, a surgical grasping device, etc.

Figure 3:
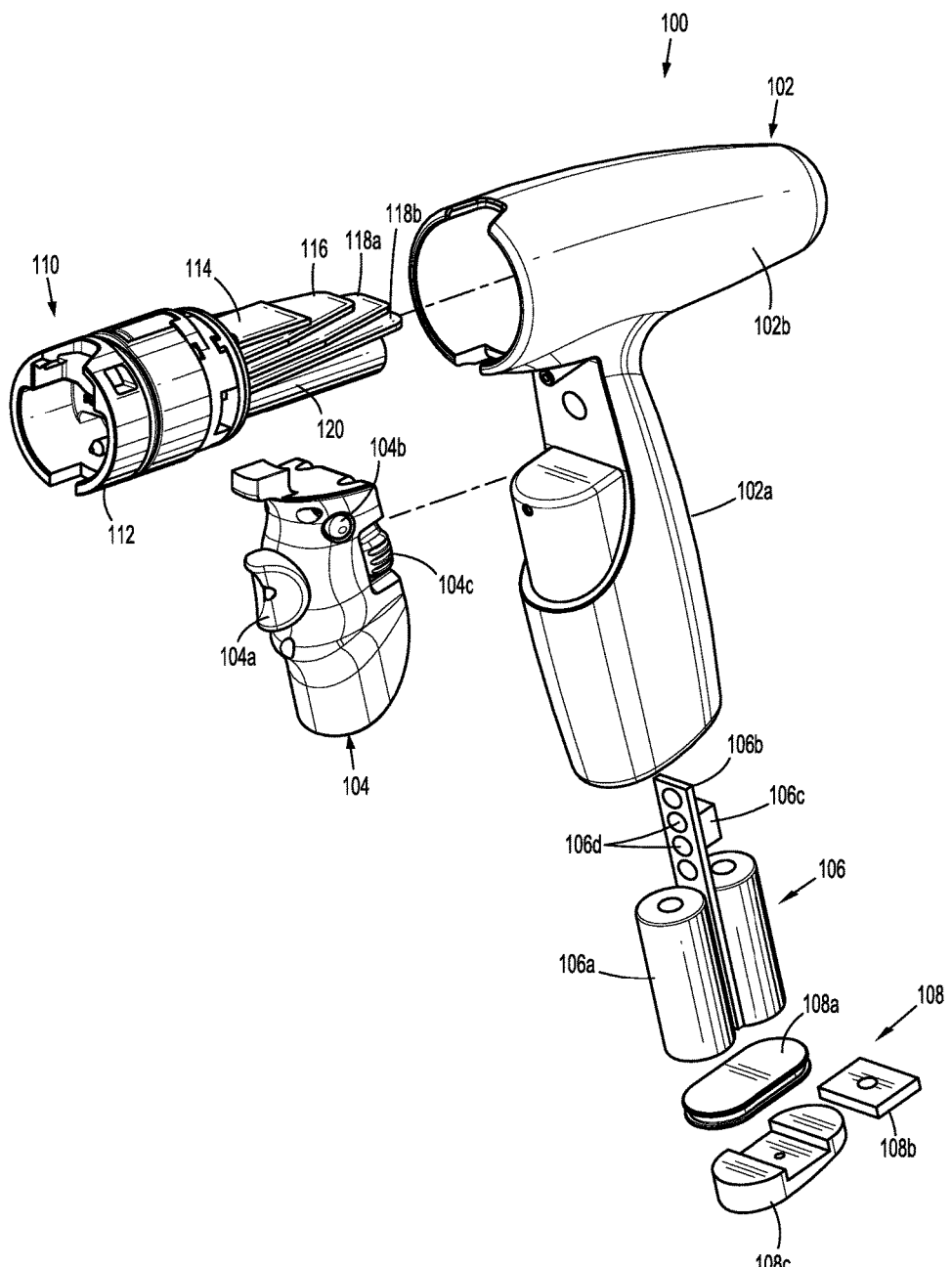
FIG. 3 is a perspective view, with parts separated, of a handle assembly of the electromechanical surgical system of FIG. 1.

As seen in FIG. 3, handle assembly 100 includes a handle housing 102 having a handle portion 102a and a body portion 102b extending transverse from body portion 102a. A switch block assembly 104 is removably mounted on handle portion 102a and includes various switches or actuators 104a-104c that are operable to activate some function of electromechanical surgical system 10 such as firing, rotation, articulation, and/or providing a safety lock. For example, as described in greater detail below, actuator 104a can be depressed to fire loading unit 300 (and/or end effector 302) while the components of electromechanical surgical system 10 are coupled together. In embodiments, one or more of actuators 104a-104c may be coupled to or support one or more magnets (not shown) for creating a magnetic field and/or communicating electrical signals to sensors disposed within handle and/or body portions 102a, 102b of handle assembly 100. A power assembly 106 is mounted in handle portion 102a by a sealing assembly 108. Power assembly 106 includes a battery pack 106a and a circuit board 106b that are electrically coupled to one another. Circuit board 106b can support any number or type of electrical components such as inductors 106c, sensors 106d (e.g., Hall Effect sensors), wires, chips, resistors, capacitors or the like. These electrical components may be in electrical communication with each other and/or with actuators 104a-104c.

Sealing assembly 108 is mounted to handle portion 102a and includes a sealing plate 108a, a twist lock plate 108b, and a cover plate 108c that couple together to support power assembly 106 within handle portion 102a.

A drive assembly 110, described in greater detail below, is supported in body portion 102b and includes a handle mount 112 that supports one or more antennae 114, 116 and one or more circuit boards 118a, 118b (e.g., with any number and/or type of electrical components as described above with respect to circuit board 106b) that are in electrical communication with power assembly 106. The antennae 114, 116 and/or circuit boards 118a, 118b (and/or circuit board 106b) may be wired and/or wirelessly coupled to one or more of any of the components of electromechanical surgical system 10. Handle mount 112 further supports a motor assembly 120 that is electrically coupled to antennae 114, 116 and/or circuit boards 118a, 118b which may function to activate motor assembly 120, or components thereof, upon actuation of one or more of switches 104a-104c of switch block assembly 104. The one or more antennae 114, 116 can be configured to electrically communicate (e.g., send and/or receive signals) with a remote system such as a cloud (not shown) and/or other remote system (e.g., a computer, robot, etc.).

Figure 4:
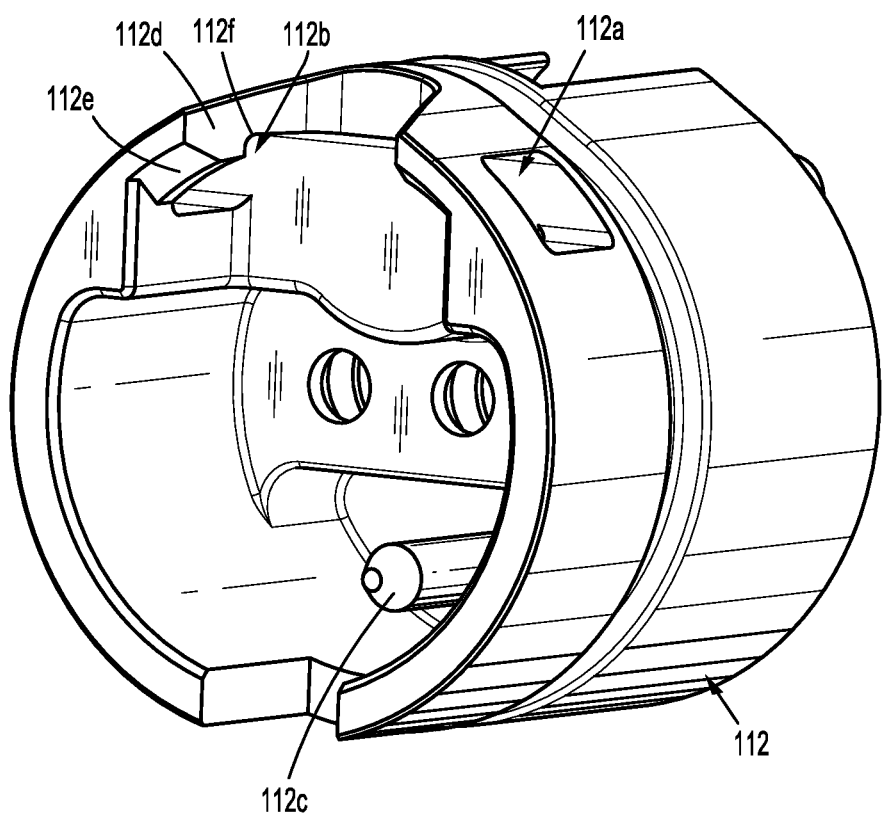
FIG. 4 is an enlarged perspective view of a handle mount of the handle assembly of FIG. 3.
Figure 5:
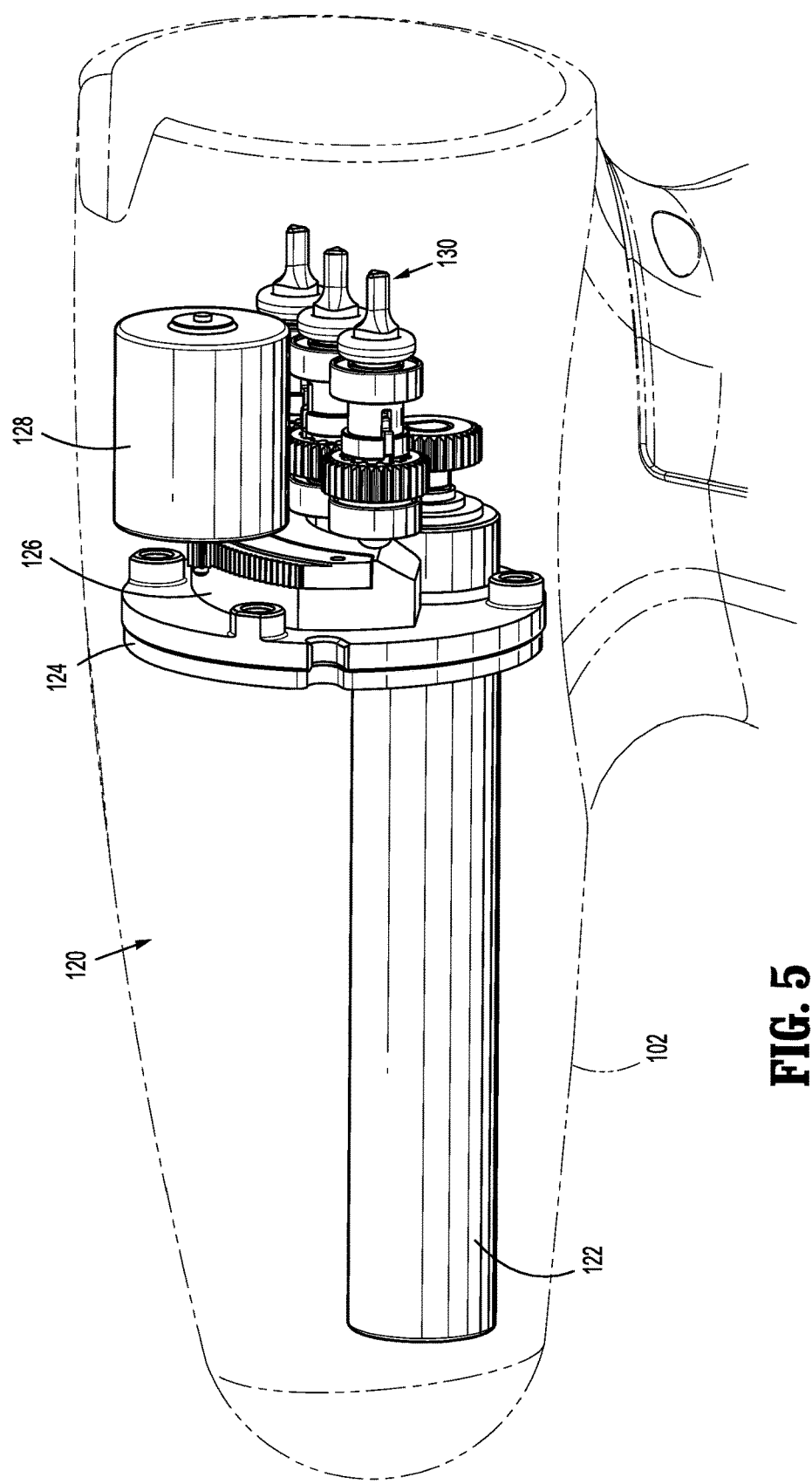
FIG. 5 is an enlarged perspective view of a motor assembly of the handle assembly of FIG. 3 with a handle housing of the handle assembly shown in phantom for clarity.
Figure 6:
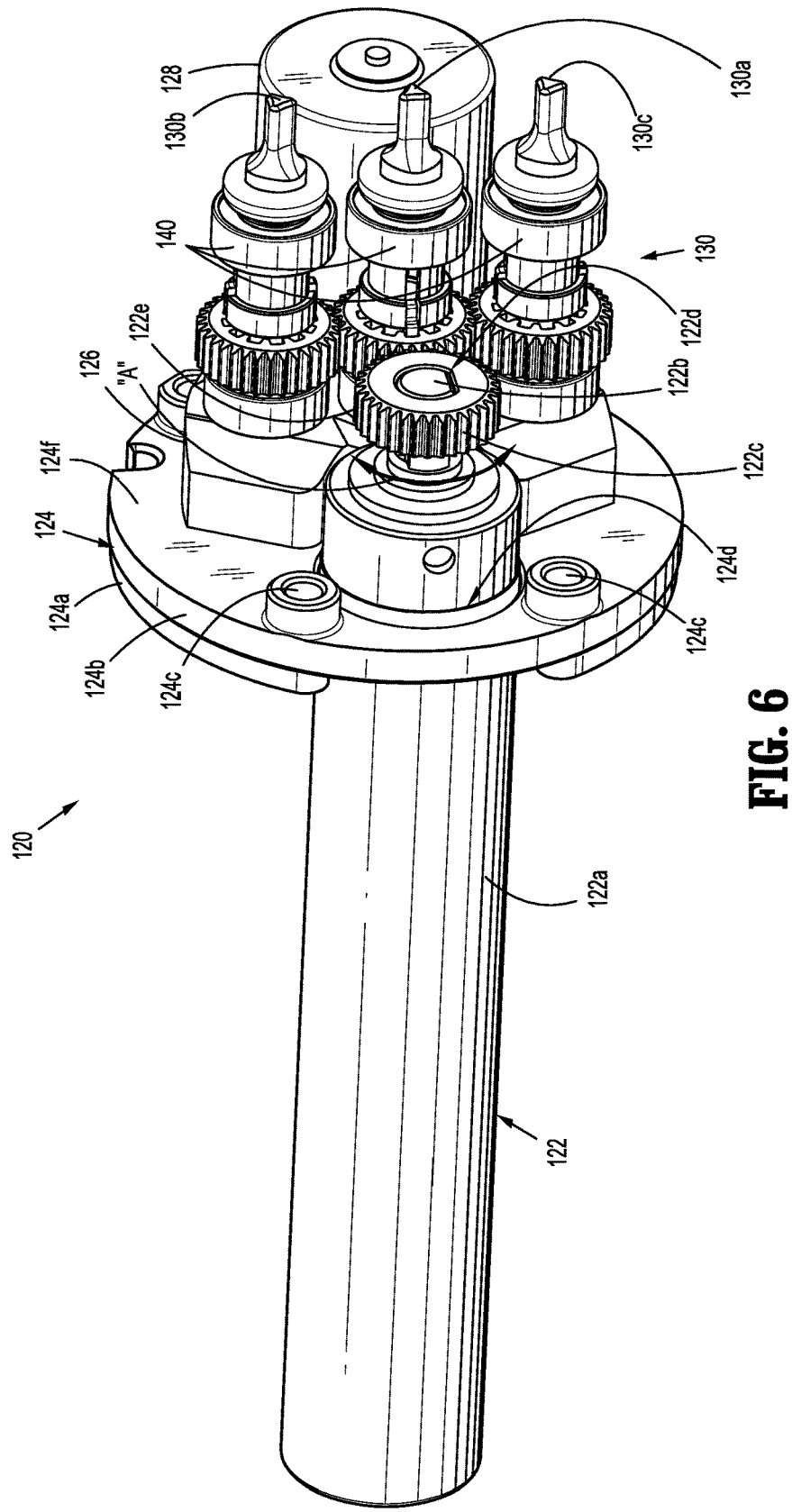
FIG. 6 is an enlarged perspective view of the motor assembly of FIG. 5.

As seen in FIG. 4, handle mount 112 defines first and second windows 112a, 112b therethrough and an alignment pin 112c that extends distally therefrom. An engagement tooth 112d is positioned distal to each of the respective first and second windows 112a, 112b. Each engagement tooth 112d defines a distal surface 112e that tapers proximally towards its respective window 112a, 112b. Each engagement tooth 112d further includes a proximal shoulder 112f.

For a more detailed description of similar surgical devices and components thereof that can be combined and/or interchanged with, or adapted for use with, the presently described electromechanical surgical systems 10, or components thereof, reference can be made to U.S. provisional patent application Ser. No. 62/066,996, filed on Oct. 22, 2014, International Publication. No. WO 2009/039506, and U.S. Patent Application Publication No. 2011/0121049, the entire contents of each of which are incorporated by reference herein.

Turning now to FIGS. 5-9, motor assembly 120 includes a drive motor assembly 122, mounting plates 124 supported on drive motor assembly 122, a selector cam 126 rotatably supported on drive motor assembly 122 adjacent mounting plates 124, a selector motor 128 coupled to selector cam 126, and an output assembly 130 coupled to drive motor assembly 122.

Drive motor assembly 122, which is electrically coupled to circuit boards 106b, 118a, 118b and/or antenna 116, includes a single motor 122a, a shaft 122b that extends distally from motor 122a, and a drive gear 122c. Shaft 122b has a non-circular cross-section. The cross-section of shaft 122b may have any suitable cross-sectional configuration (e.g., star, triangle, hexalobular, D-shape, etc.). Drive gear 122c defines an opening 122d that receives shaft 122b of drive motor assembly 122 so that drive gear 122c rotates with shaft 122b, as indicated by arrow "A," upon actuation of motor 122a. Opening 122d may have any suitable configuration. In embodiments, opening 122d complements the cross-section of shaft 122b. Drive gear 122c further defines teeth 122e around an outer surface thereof that engage output shaft assembly 130 to impart drive force from motor 122a thereon.

Mounting plates 124 include first and second mounting plates 124a, 124b that are secured together using any known fastening technique such as welding, fastening, press-fit, etc. For example, first and second mounting plates 124a, 124b can be secured together by fasteners 124c. Drive motor assembly 122 extends through an enlarged first aperture 124e formed in first mounting plate 124a and a second aperture 124d defined in second mounting plate 124b to receive motor 122a of drive motor assembly 122 therein and to support drive motor assembly 122.

Figure 9:
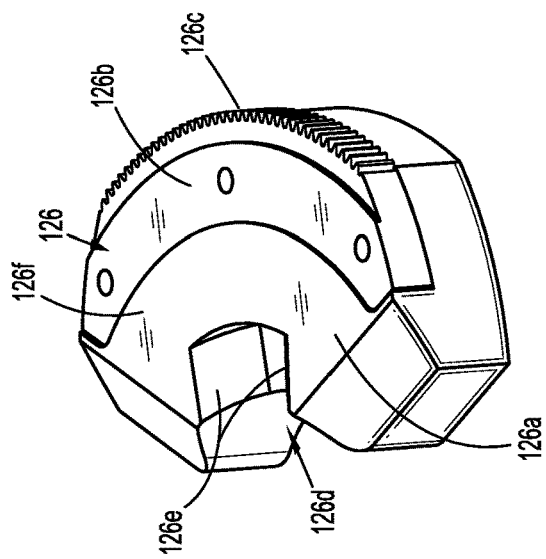
FIG. 9 is an enlarged perspective view of a selector cam of the motor assembly of FIGS. 5-7.

Selector cam 126 is coupled to selector motor 128 and mounted on drive motor assembly 122 adjacent to, and in contact with, a distal surface 124f of second mounting plate 124b. As indicated by arrow "B" seen in FIG. 7, selector cam 126 rotates radially around drive motor assembly 122, as described in greater detail below. With reference to FIG. 9, selector cam 126 includes a body portion 126a and a gear portion 126b. Gear portion 126b is secured to, or otherwise formed in, body portion 126a and includes teeth 126c extending therefrom. Teeth 126c are shown arranged in an arcuate configuration about gear portion 126b, but may be arranged in any suitable configuration. Body portion 126a of selector cam 126 defines a recess 126d having tapered sidewalls 126e. Body portion 126a further includes a compression surface 126f positioned between gear portion 126b and recess 126d.

Figure 7:
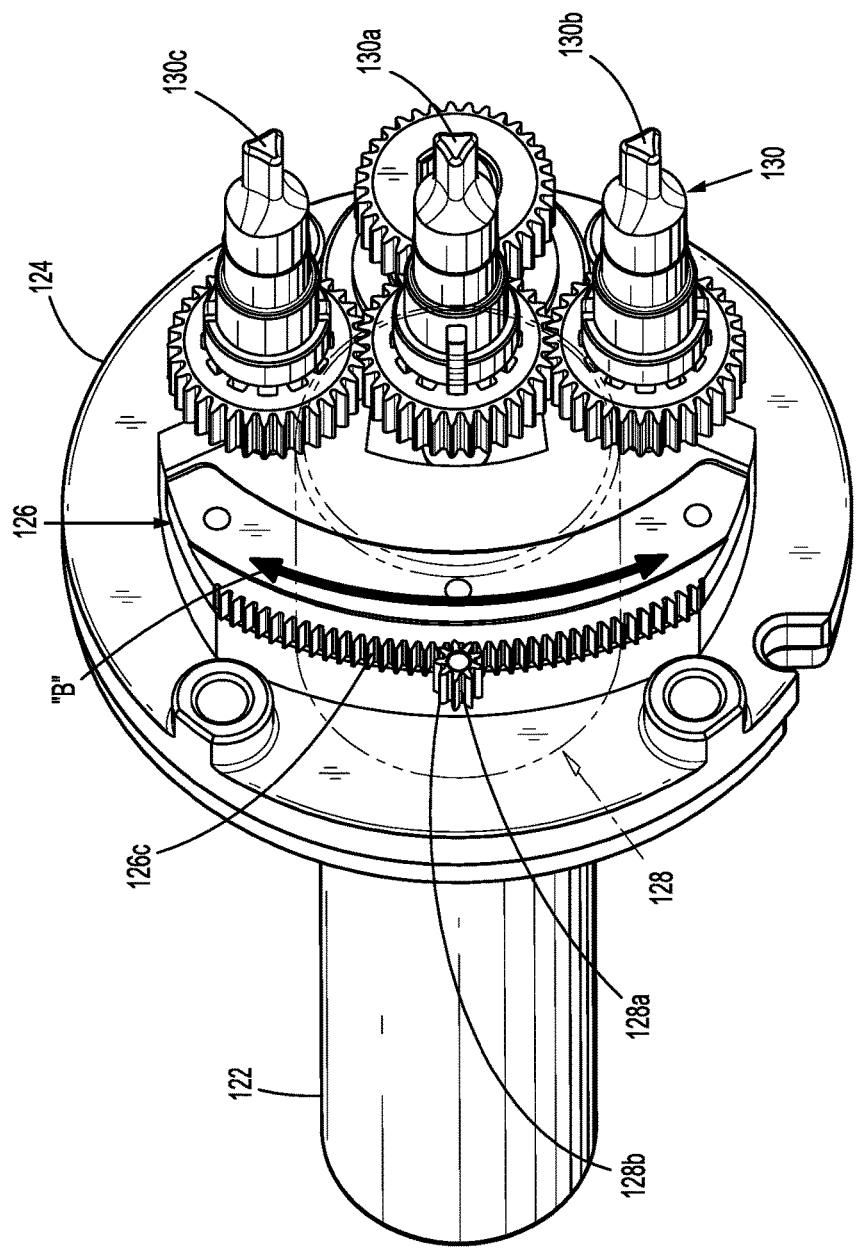
FIG. 7 is an enlarged perspective view of the motor assembly of FIGS. 5 and 6 with a selector motor thereof shown in phantom for clarity.

As seen in FIG. 7, selector motor 128 includes, or rotatably supports, a selector gear 128a having teeth 128b that are engaged with teeth 126c of selector cam 126. Selector motor 128 rotates selector gear 128a to rotate selector cam 126 between first, second, and third positions about drive motor assembly 122, as described in greater detail below.

Figure 8:
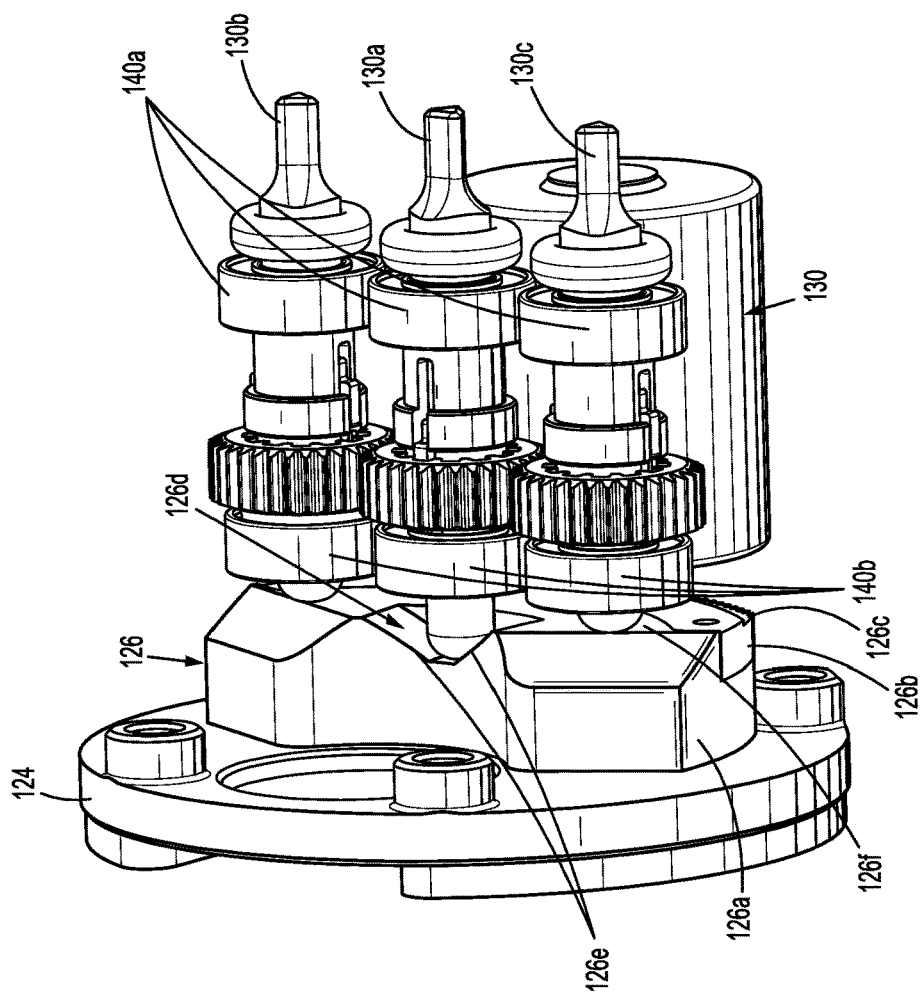
FIG. 8 is an enlarged perspective view of a distal portion of the motor assembly of FIGS. 5 and 6 with a drive motor thereof removed for clarity.

Referring also to FIG. 8, motor assembly 120 includes an output assembly 130 having a first output assembly 130a, a second output assembly 130b, and a third output assembly 130c.

Figure 12:
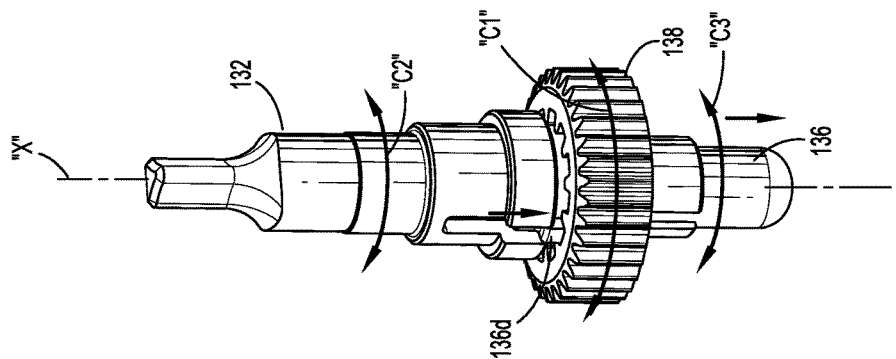
FIGS. 11 and 12 are progressive views of the output assembly of FIG. 10 illustrating the output assembly moving between first and second positions.
Figure 11:
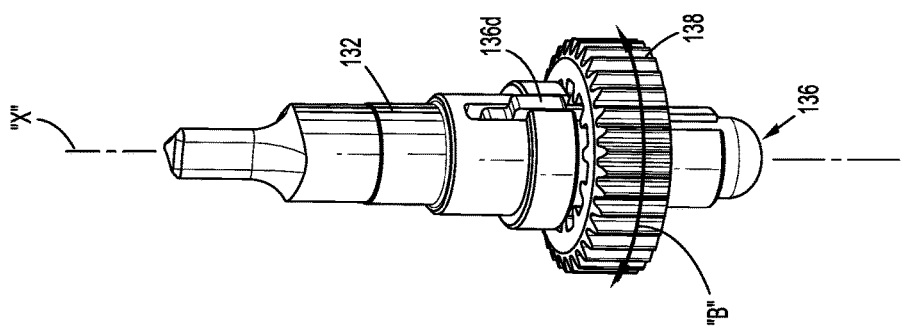
Figure 10:
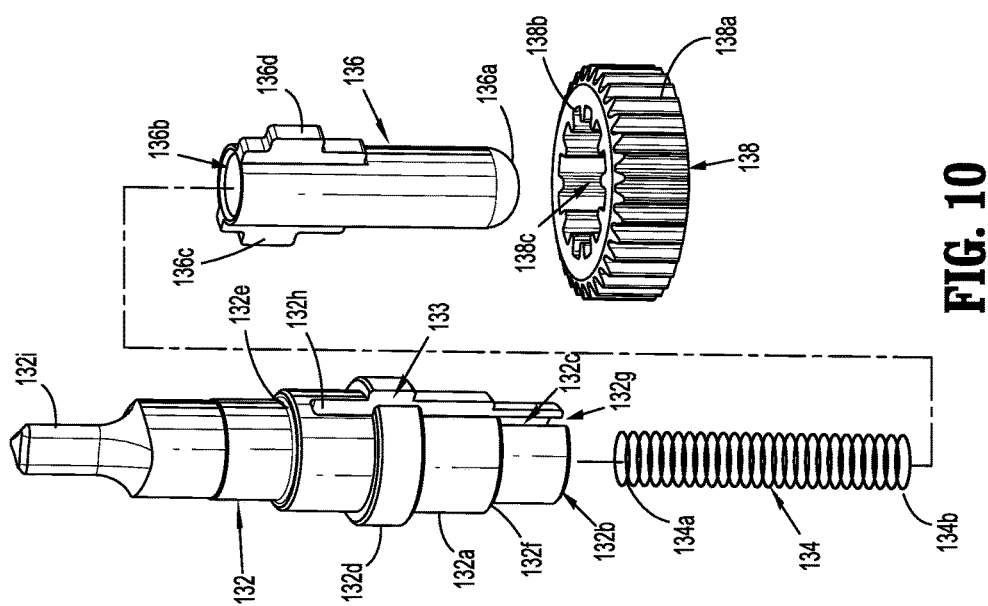
FIG. 10 is a perspective view, with parts separated, of an output assembly of the motor assembly of FIGS. 5-7.

With referenced to FIGS. 10-12, each of the first, second, and third output assemblies 130a, 130b, 130c (see FIGS. 7 and 8) defines a longitudinal axis "X" and includes a respective output shaft 132, spring 134, engagement key 136, and output gear 138. Output shaft 132 includes a shaft body 132a that defines a spring bore 132b therein and a slot 132c therealong. Spring bore 132b of output shaft 132 receives a first end 134a of spring 134 therein. Shaft body 132a of output shaft 132 includes first, second, and third annular shoulders 132d, 132e, 132f that extend radially around an outer surface thereof at spaced apart locations relative to one another. First annular shoulder 132d of shaft body 132a is positioned between second and third shoulders 132e, 132f and functions to limit axial movement of output gear 138 along shaft body 132a. Second annular shoulder 132e of shaft body 132a is positioned distal to first and third annular shoulders 132d, 132f and functions to support a distal bearing 140a thereon. Third annular shoulder 132e of shaft body 132a is positioned proximal to first and second shoulders 132f and functions to support a proximal bearing 140b thereon (see, e.g., FIG. 8). Slot 132c of output shaft 132 extends from an open proximal end 132g of shaft body 132a that receives spring 134, and through shoulder 132d to separate shoulder 132d into two separate and discrete sections with a coupling region 133 for engagement key 136 defined therebetween. Slot 132c of output shaft 132f opens through opposite side surfaces of shaft body 132a and includes a closed distal end 132h adjacent to, and proximal of, second shoulder 132e.

Output shaft 132 includes a driver head 132i that extends distally from shaft body 132a. Driver head 132i can have any suitable non-circular configuration such as a triangular configuration, square configuration, hexalobular configuration, etc.

Engagement key 136 of each output assembly 130 includes a rounded tip 136a at a proximal end thereof and defines a spring bore 136b in a distal end thereof. Spring bore 136b receives a second end 134b of spring 134 therein to support spring 134 between output shaft 132 and engagement key 136. Engagement key 136 further includes flanges 136c, 136d that extend laterally outward from side surfaces of the distal end of engagement key 136. Flanges 136c, 136d of engagement key 136 are slidable through slot 132c of output shaft 132 on opposite sides of output shaft 132. Spring 134 is configured to bias engagement key 136 in a proximal direction (e.g., away from output shaft 132) toward selector cam 126.

Output gear 138 of each output assembly 130 includes outer teeth 138a that extend from an outer surface thereof, and inner teeth 138b that extend from an inner surface thereof into an opening 138c defined through output gear 138. Adjacent inner teeth 138b of output gear 138 are spaced to selectively receive flanges 136c, 136d of engagement key 136 therein.

As described in greater detail below, in a disengaged position (e.g., unlocked) of engagement key 136 with respect to output gear 138, flanges 136c, 136d of engagement key 136 are longitudinally offset from, and distal to, inner teeth 138b of output gear 138 relative to longitudinal axis "X," as seen in FIG. 11, such that output gear 138 can rotate about, and relative to, longitudinal axis "X," engagement key 136, and output shaft 132, as indicated by arrows "B." Specifically, output gear 138 is independent of engagement key 136 and output shaft 132, when engagement key 136 is in the disengaged position.

In an engaged position (e.g., locked) of engagement key 136 with respect to output gear 138, as seen in FIG. 12, flanges 136c, 136d of engagement key 136 are partially disposed between inner teeth 138b of output gear 138 (e.g., partially longitudinally aligned relative to longitudinal axis "X") while partially positioned within coupling region 133 of shoulder 132d of output shaft 132. In the engaged position of engagement key 136, output shaft 132 and output gear 138 are locked and movable together. More specifically, output shaft 132, engagement key 136, and output gear 138 rotate together about longitudinal axis "X," as indicated by arrows "C1," "C2," and "C3."

Figure 13:
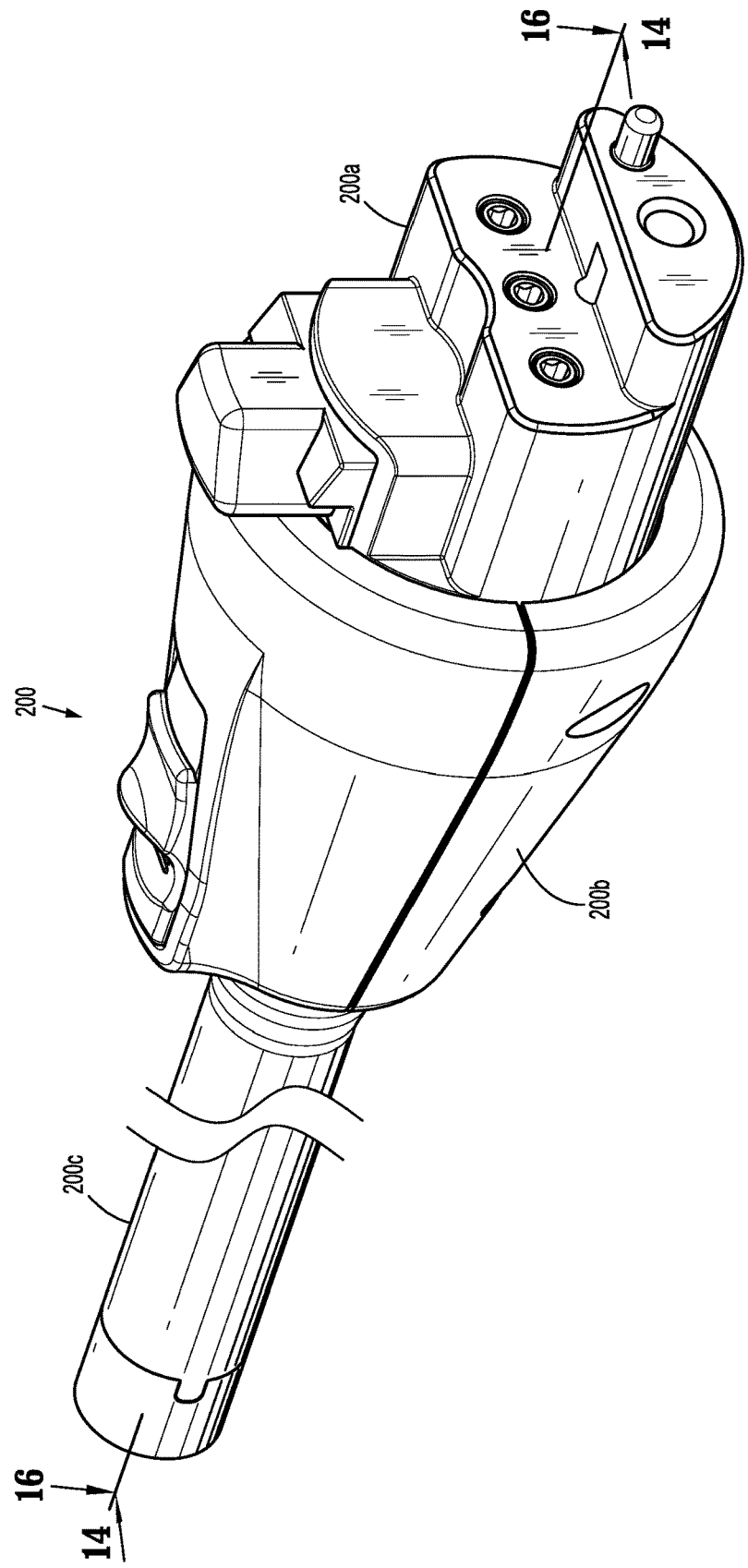
FIG. 13 is an enlarged, rear, perspective view of an adapter assembly of the electromechanical surgical system of FIG. 1.

Turning now to FIG. 13, adapter assembly 200 includes a proximal housing 200a at a proximal end of adapter assembly 200. The proximal end of proximal housing 200a selectively secures to a distal end of handle assembly 100. Adapter assembly 200 includes a distal housing 200b that extends distally from proximal housing 200 and an outer tube 200c that extends distally from distal housing 200b to a distal end.

Figure 14:
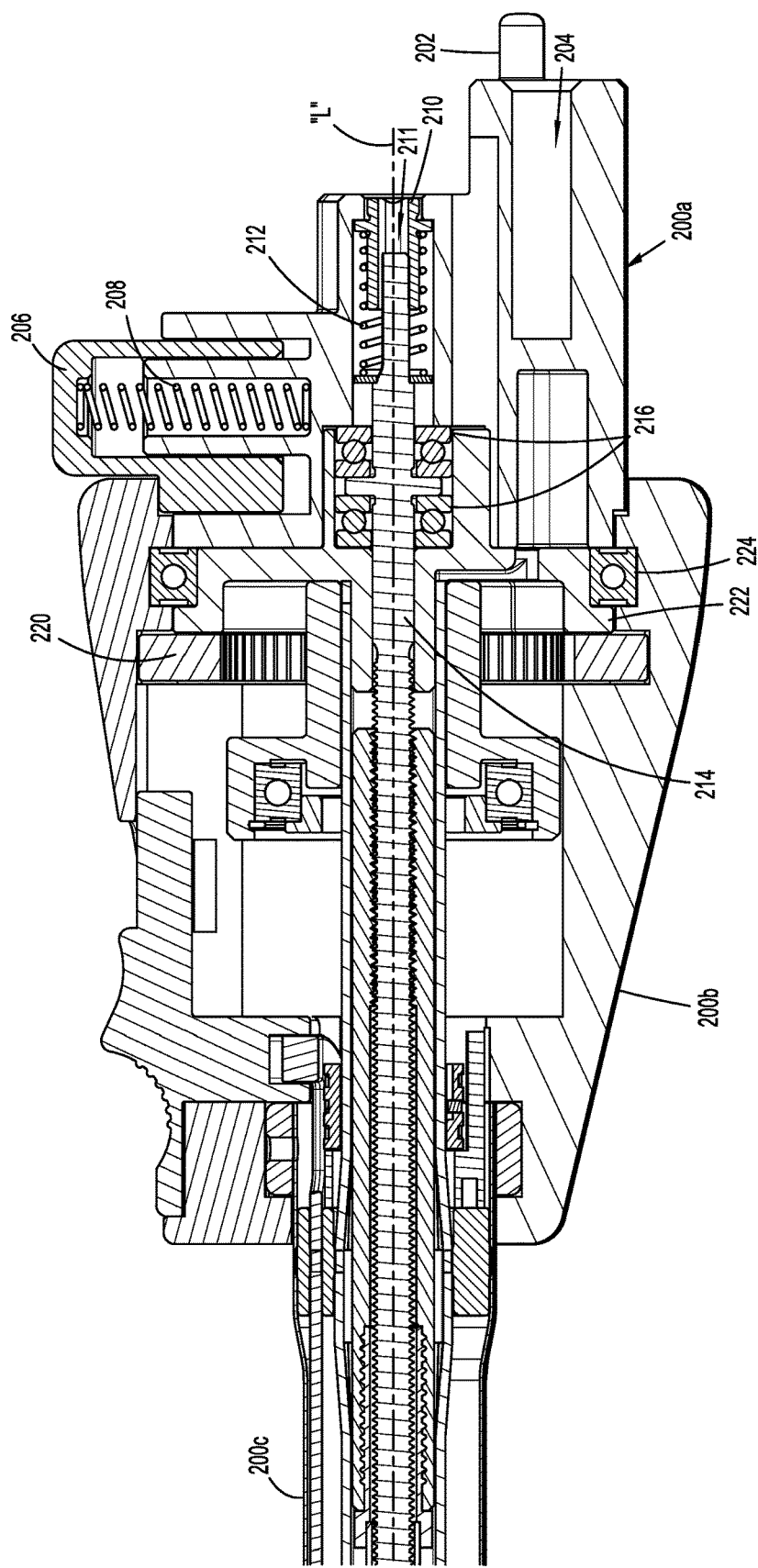
FIG. 14 is a cross-sectional view of the adapter assembly of FIG. 13 as taken along section line 14-14 shown in FIG. 13.
Figure 15:
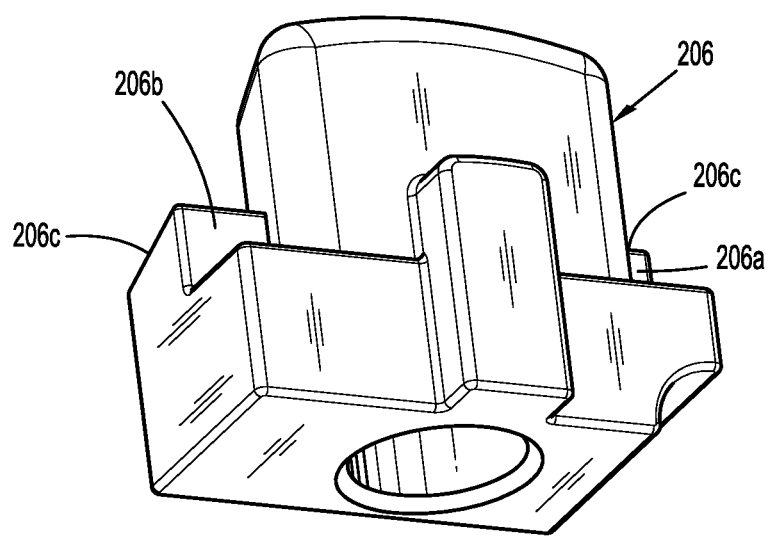
FIG. 15 is an enlarged perspective view of an adapter release button of the adapter assembly of FIG. 13.
Figure 19:
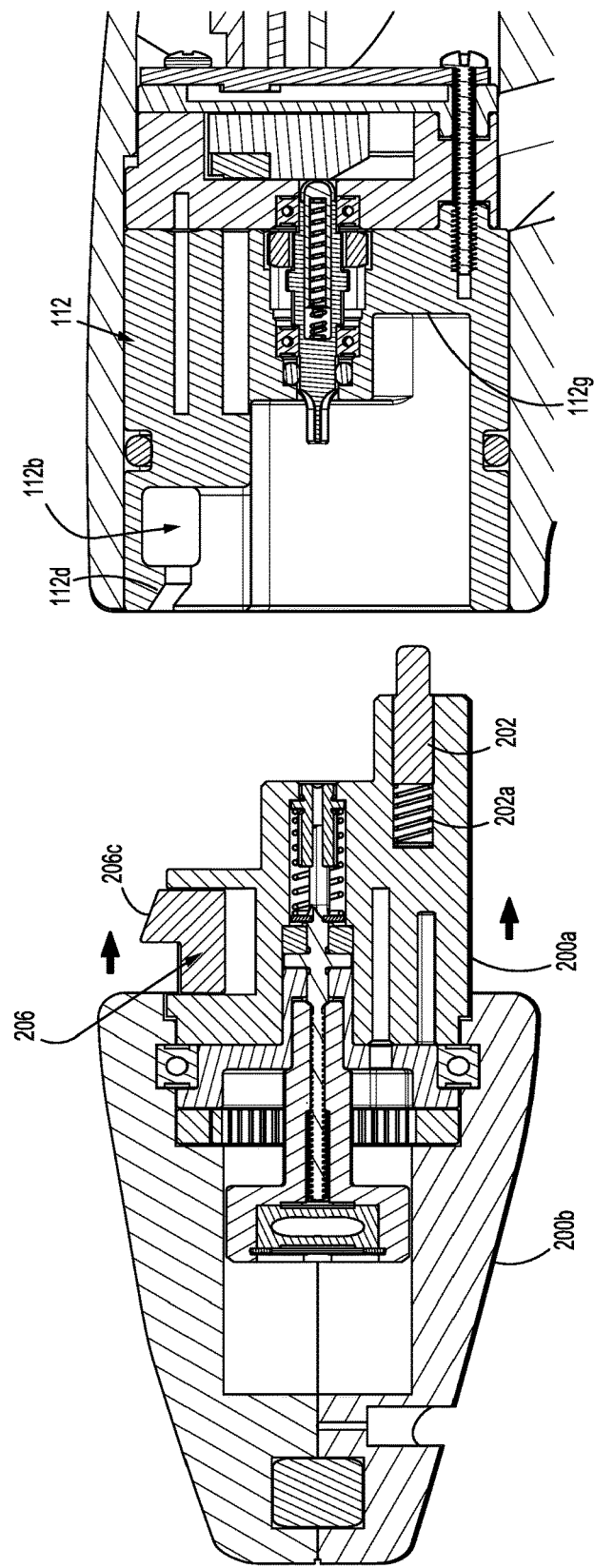
Figure 20:
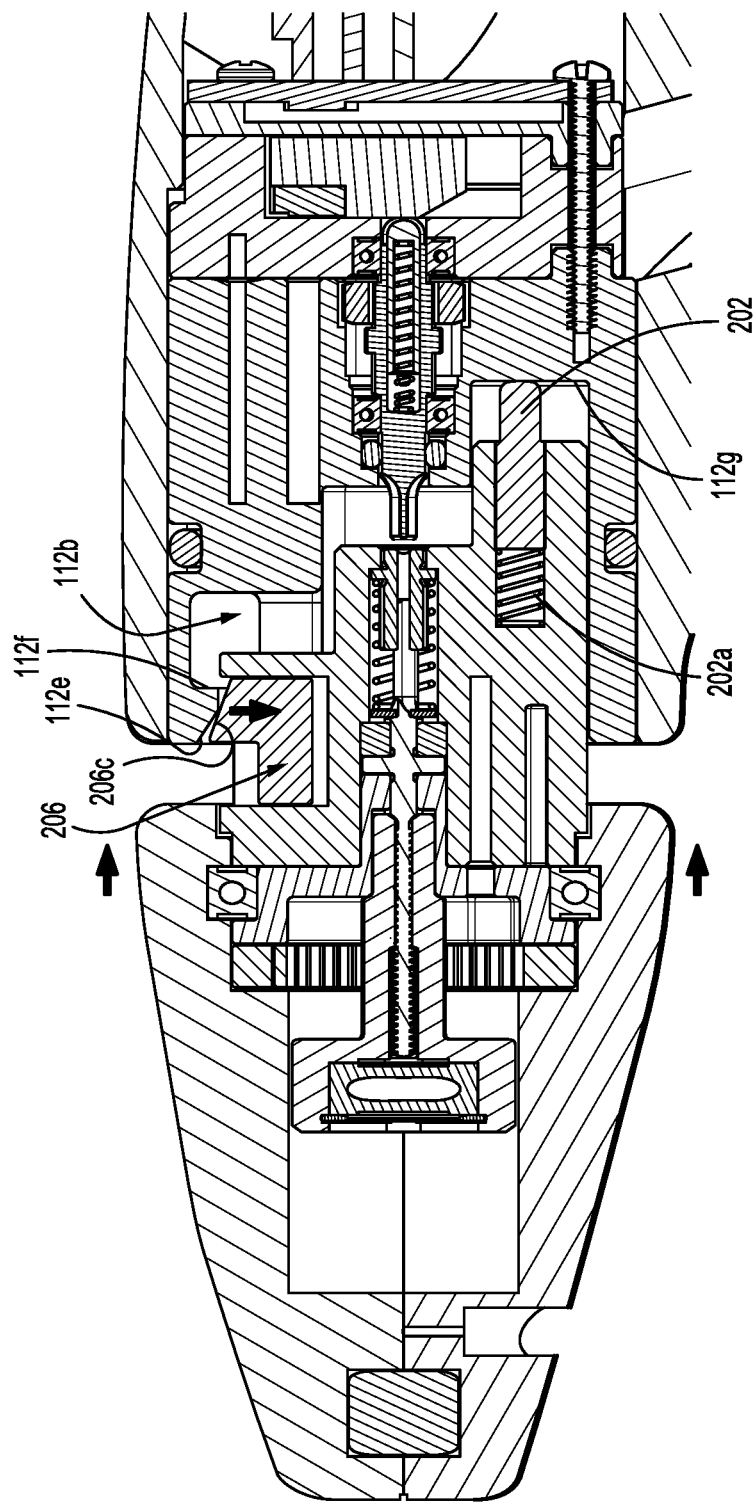
Figure 21:
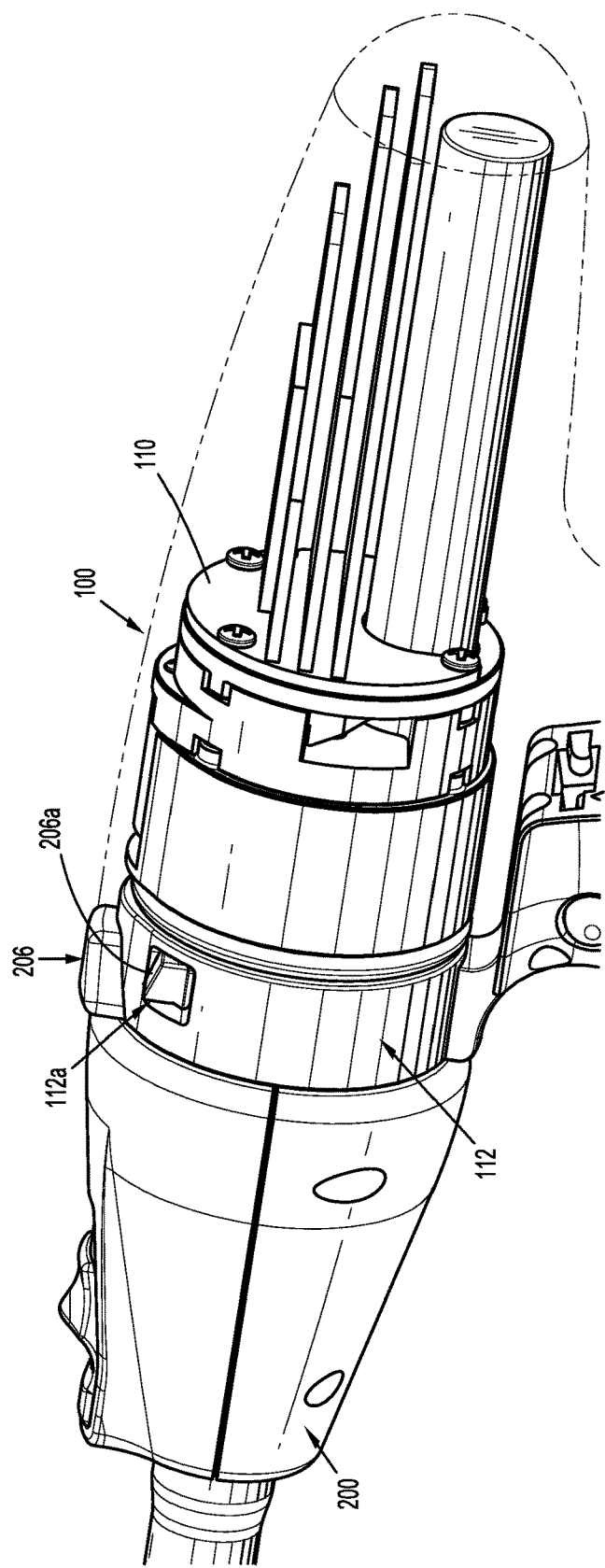
Figure 22:
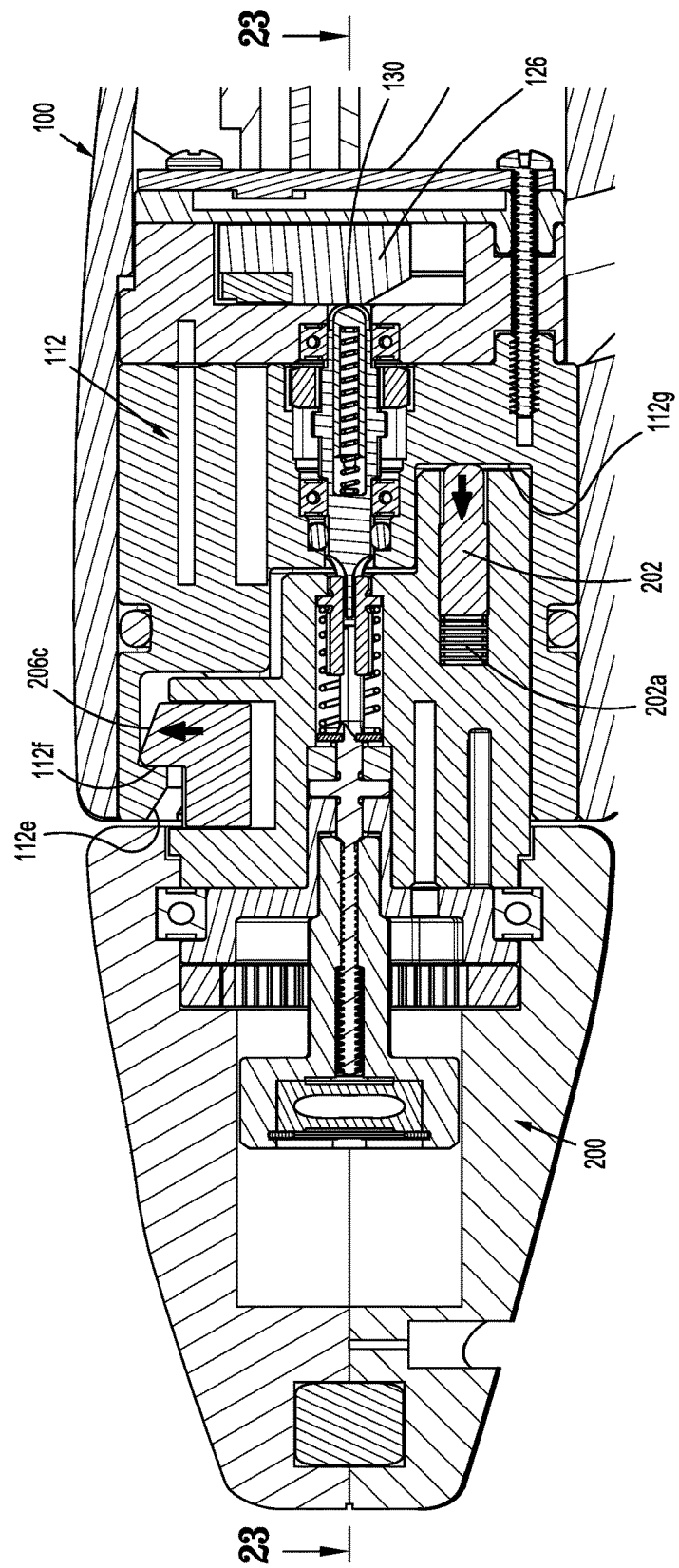
Figure 23:
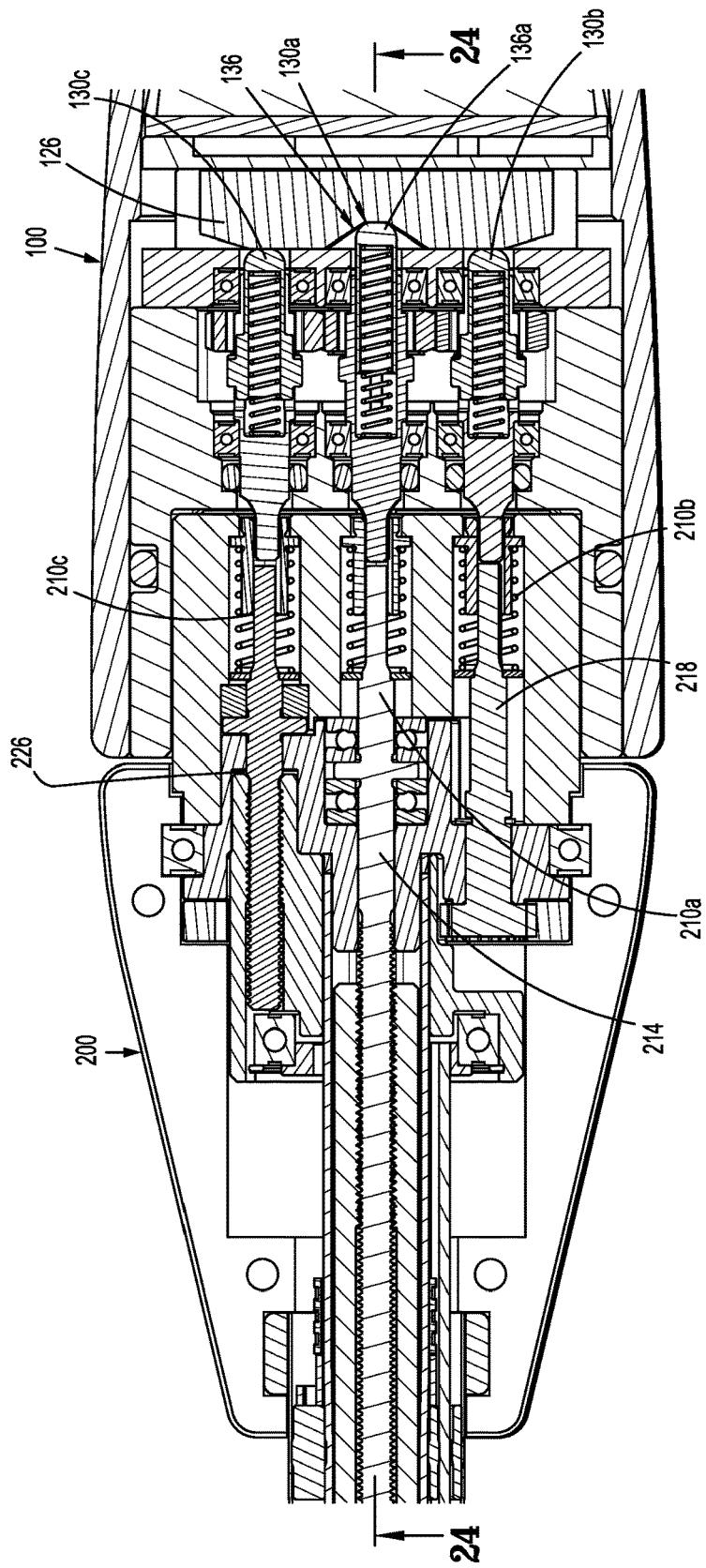
Figure 24:
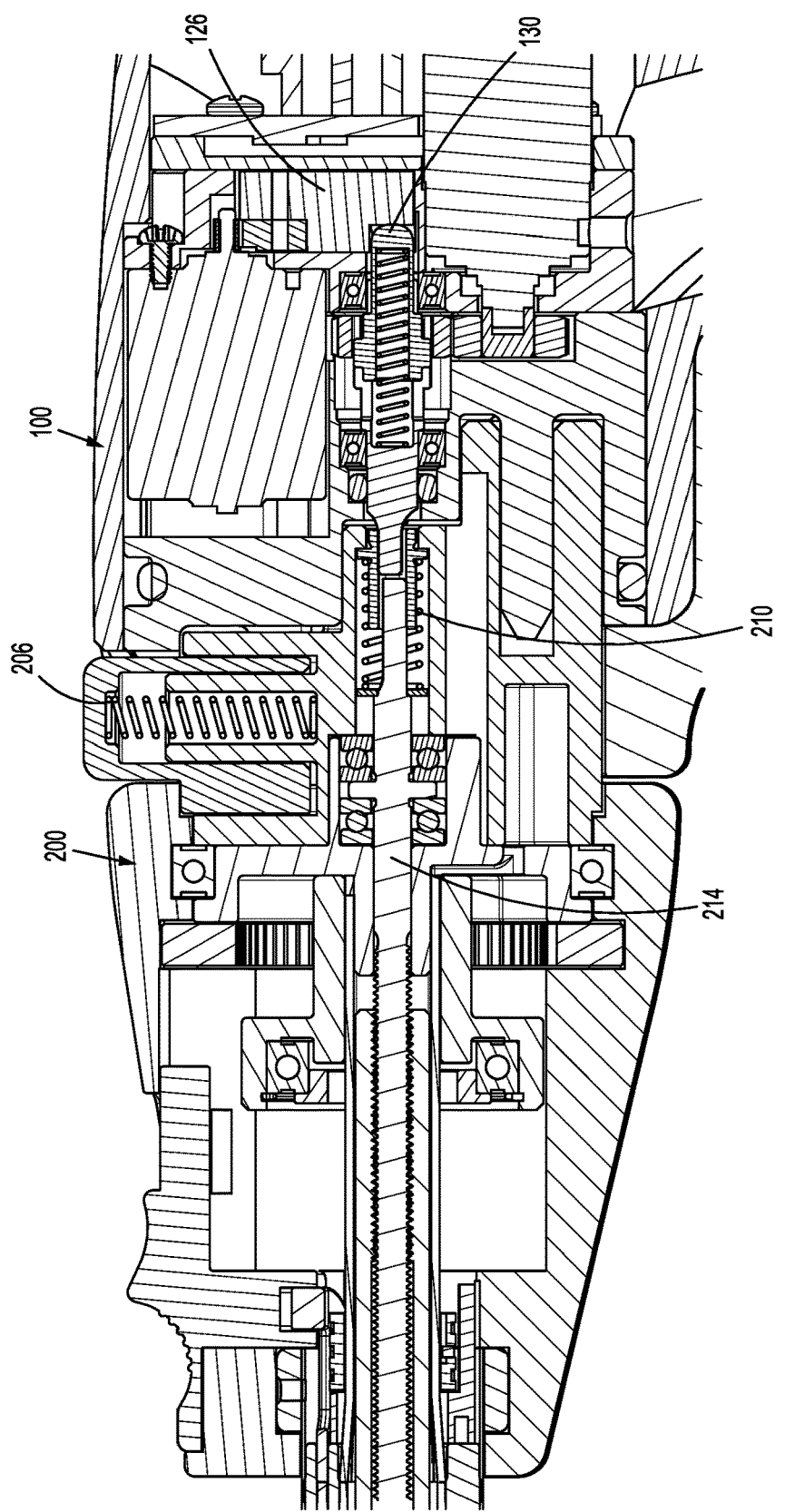

With reference to FIG. 14, proximal housing 200a of adapter assembly 200 supports an ejector pin 202 that is spring biased by a spring 202a (see FIG. 19). Proximal housing 200a defines an alignment bore 204 that receives alignment pin 112c of handle mount 112 during coupling of adapter assembly 200 to handle assembly 100 (see FIG. 17). Proximal housing 200a further supports a spring loaded button 206 that is spring biased by a spring 208. As seen in FIG. 15, spring loaded button 206 includes nubs 206a, 206b that extend to angled surfaces 206c. Nubs 206a, 206b are receivable within windows 112a, 112b of handle mount 112 (see FIG. 4), respectively, to secure adapter assembly 200 to handle assembly 100 as described in greater detail below.

Figure 16:
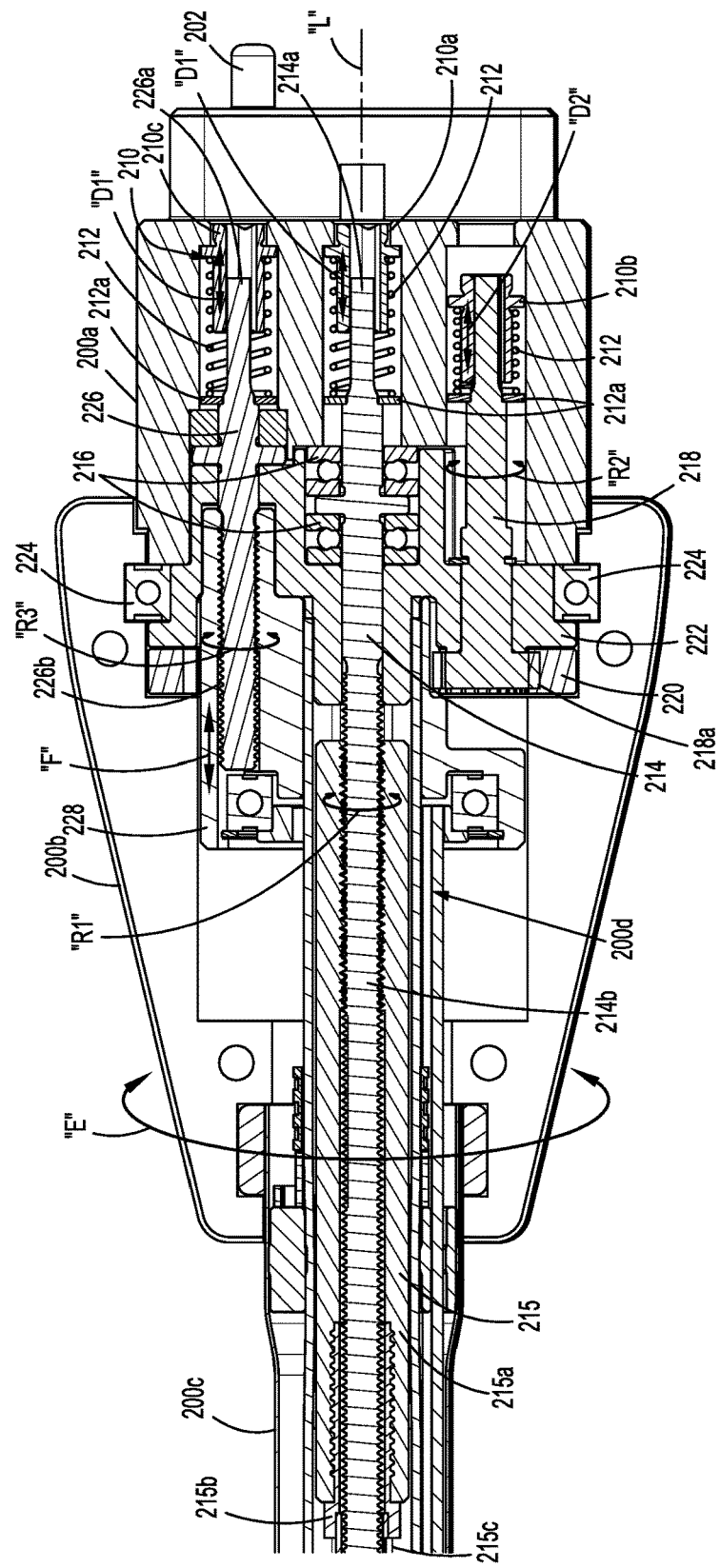
FIG. 16 is a cross-sectional view of the adapter assembly of FIG. 13 as taken along section line 16-16 shown in FIG. 13.
Figure 17:
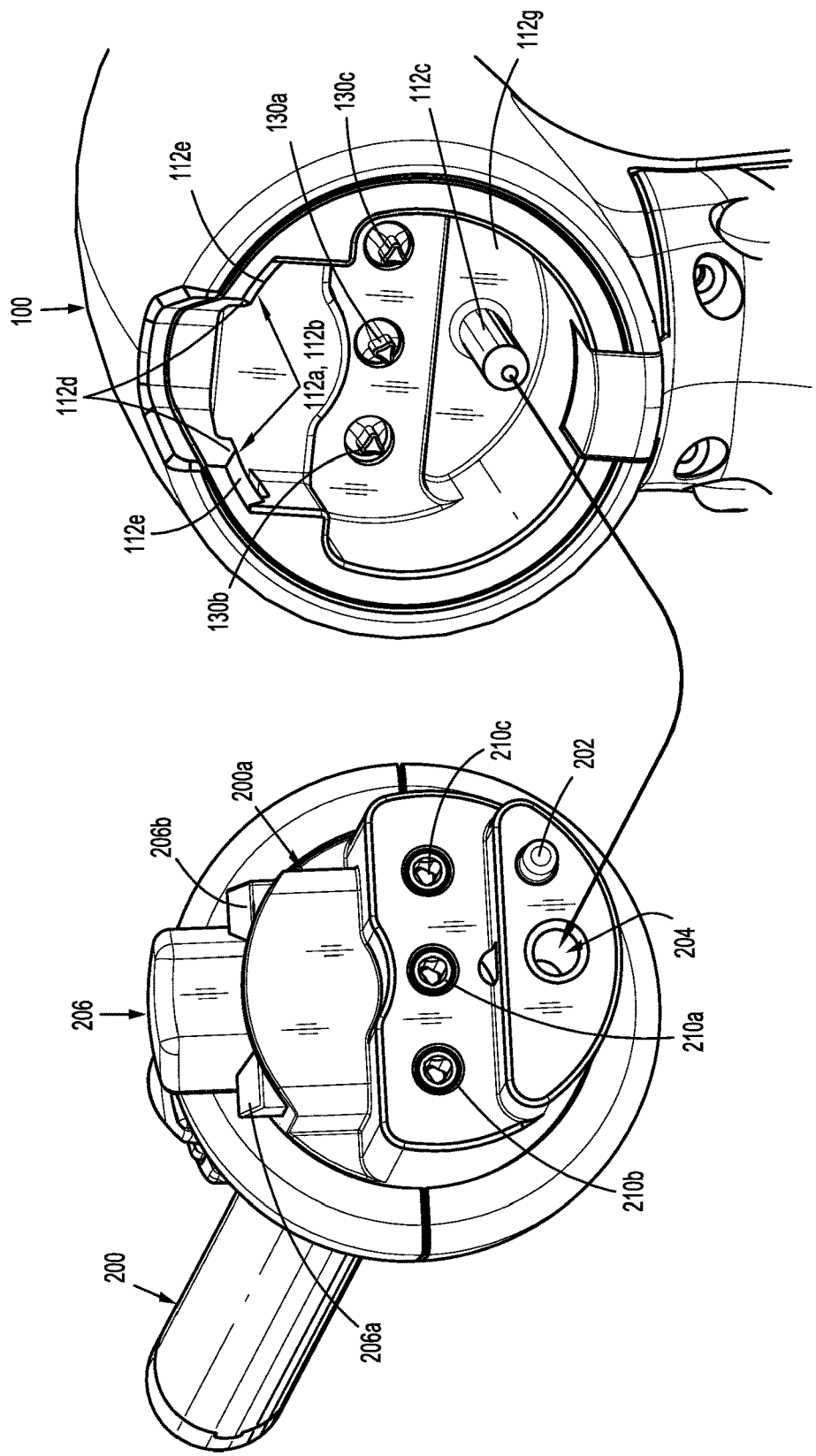
FIG. 17 is a perspective view, with parts separated, of the handle and adapter assemblies of FIGS. 3 and 13.
Figure 18:
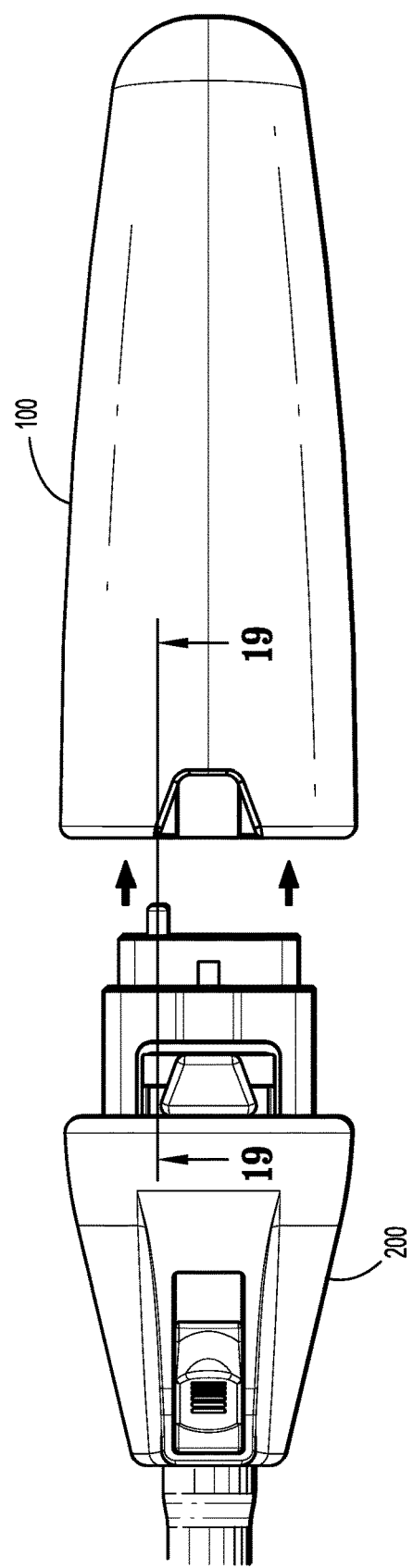
FIGS. 18-24 are progressive views showing the adapter assembly of FIG. 13 being connected to the handle assembly of FIG. 3.

Referring also to FIG. 16, input couplers 210 of adapter assembly 200 include first, second, and third input couplers 210a, 210b, 210c that are supported by proximal housing 200a and are spring biased in a proximal direction, as indicated by arrows "D 1," by springs 212 coupled to rotation mounts 212a. As indicated by arrows "D2," springs 212 can be compressed in a distal direction against biasing forces of springs 212. As seen in FIG. 14, each input coupler 210 defines a non-circular passage 211 therethrough that may have any suitable cross-sectional configuration (e.g., star, triangle, hexalobular, D-shape, etc.). With reference to FIG. 17, first, second, and third input couplers 210a, 210b, 210c are positioned to complement output shafts 130a, 130b, 130c of handle assembly 100, respectively.

With continued reference to FIG. 16, first input coupler 210a is coupled to a proximal segment 214a of a firing shaft 214 of adapter assembly 200 and is rotatable with first input coupler 210a, as indicated by arrows "R1." Firing shaft 214 is supported by bearings 216 disposed in distal housing 200b and includes a threaded distal segment 214b having proximal and distal ends. The proximal end of threaded distal segment 214b is coupled to a threaded sleeve assembly 215, and the distal end of threaded distal segment 214b is coupled to loading unit 300 (and/or end effector 302).

Threaded sleeve assembly 215 includes a support sleeve 215a threadably coupled to a tension sleeve 215b. Tension sleeve 215b can be coupled to connecting members 215c (e.g., cables, rods, etc.) that extend distally to a distal end of outer tube 200c to manipulate the distal end of outer tube 200c of adapter assembly 200 when coupled to loading unit 300 (and/or end effector 302). For example, connecting members 215c may couple to a gimbal (not shown) or the like to facilitate articulation of loading unit 300 (and/or end effector 302) relative to adapter assembly 200. A more detailed description of an exemplary gimbal that can be used with, or adapted for use with, the presently described electromechanical surgical system 10, reference can be made to U.S. patent application Ser. No. 14/257,063, filed on Apr. 21, 2014, the entire contents of which are hereby incorporated by reference herein.

Second input coupler 210b of adapter assembly 200 is coupled to a rotation shaft 218 of adapter assembly 200 and, as indicated by arrows "R2," rotation shaft 218 is rotatable with second input coupler 210b. Rotation shaft 218 includes a rotation gear 218a supported on a distal end of rotation shaft 218. Rotation gear 218a is engaged with a rotation ring gear 220 secured to distal housing 200b. Rotation shaft 218 is further supported in distal housing 200b by a support frame 222 and a rotation bearing 224. Rotation bearing 224 enables distal housing 200b to rotate in response to simultaneous rotation of second input coupler 210b and rotation shaft 218. In use, with distal housing 200b secured to outer tube 200c, and outer tube 200c coupled to loading unit 300 (and/or end effector 302), rotation of distal housing 200b rotates loading unit 300 (and/or end effector 302) about longitudinal axis "L," as indicated by arrows "E."

Third input coupler 210c of adapter assembly 200 is coupled to a proximal end 226a of an articulation shaft 226 that is rotatable with third input coupler 210c, as indicated by arrows "R3." A distal end 226b of articulation shaft 226 is threadably coupled to an articulation sleeve 228 secured to a proximal end of an inner tube 200d. A distal end of inner tube 200d of adapter assembly 200 is operatively coupled to loading unit 300 (and/or end effector 302). In response to rotation of articulation shaft 226, articulation sleeve 228 is axially slidable along longitudinal axis "L," as indicated by arrows "F," to perform a function such as articulation of loading unit 300 (and/or end effector 302) relative to adapter assembly 200.

The proximal ends of threaded firing shaft 214, rotation shaft 218, and/or articulation shaft 226, may have any suitable cross-sectional configuration (e.g., star, triangle, hexalobular, D-shape, etc.) and may complement the non-circular passages 211 of respective input couplers 210 to enable input couplers 210 to slide along proximal ends of respective shafts 214, 218, 226 when springs 212 are positioned between compressed (see, e.g., spring 212 of input coupler 210b in FIG. 16) and uncompressed conditions (see, e.g., springs 212 of input couplers 210a, 210c in FIG. 16), for example, to facilitate a coupling and/or uncoupling of handle and adapter assemblies 100, 200, as described in greater detail below.

As seen in FIGS. 17-24, to secure adapter assembly 200 to handle assembly 100, components of proximal housing 200a of adapter assembly 200 are aligned with components of handle mount 112 so that handle and adapter assemblies 100, 200 can be coupled upon approximation thereof. In particular, alignment pin 112c of handle mount 112 of handle assembly 100 is received in alignment bore 204 of proximal housing 200a of adapter assembly 200 and first, second, and third output assemblies 130a, 130b, 130c of handle assembly 100 are received within first, second, and third input couplers 210a, 210b, 210c of adapter assembly 200, respectively. Further, angled surfaces 206c of spring loaded button 206 of adapter assembly 200 cam along tapered distal surfaces 112e of engagement teeth 112d of handle mount 112 as spring 208 (FIG. 14) of spring loaded button 206 compresses downwardly toward a compressed state. As ejector pin 202 contacts a compression wall 112g (see FIG. 20) of handle mount 112, spring 202a of ejector pin 202 compresses toward its compressed state. As nubs 206a, 206b of spring loaded button 206 cam past engagement teeth 112d of handle mount 112, spring 208 of spring loaded button 206 biases toward its uncompressed state so that nubs 206a, 206b of spring loaded button 206 can be received within first and second windows 112a, 112b of handle mount 112, respectively. With nubs 206a, 206b of spring loaded button 206 engaged with shoulders 112f of handle mount 112, spring bias forces imparted by spring 202a of ejector pin 202, in its compressed state, further bolster engagement by increasing contact forces between nubs 206a, 206b of spring loaded button 206 and shoulders 112f of handle mount 112 to enable adapter and handle assemblies 200, 100 to remain secured together.

To decouple handle and adapter assemblies 100, 200 from one another, spring loaded button 206 is depressed to release nubs 206a, 206b from shoulders 112f of handle mount 112 so that compression forces imparted by spring 202a of ejector pin 202 separate handle and adapter assemblies 100, 200 as spring 202a biases ejector pin 202 toward its initial extended state (e.g., uncompressed).

Figure 25:
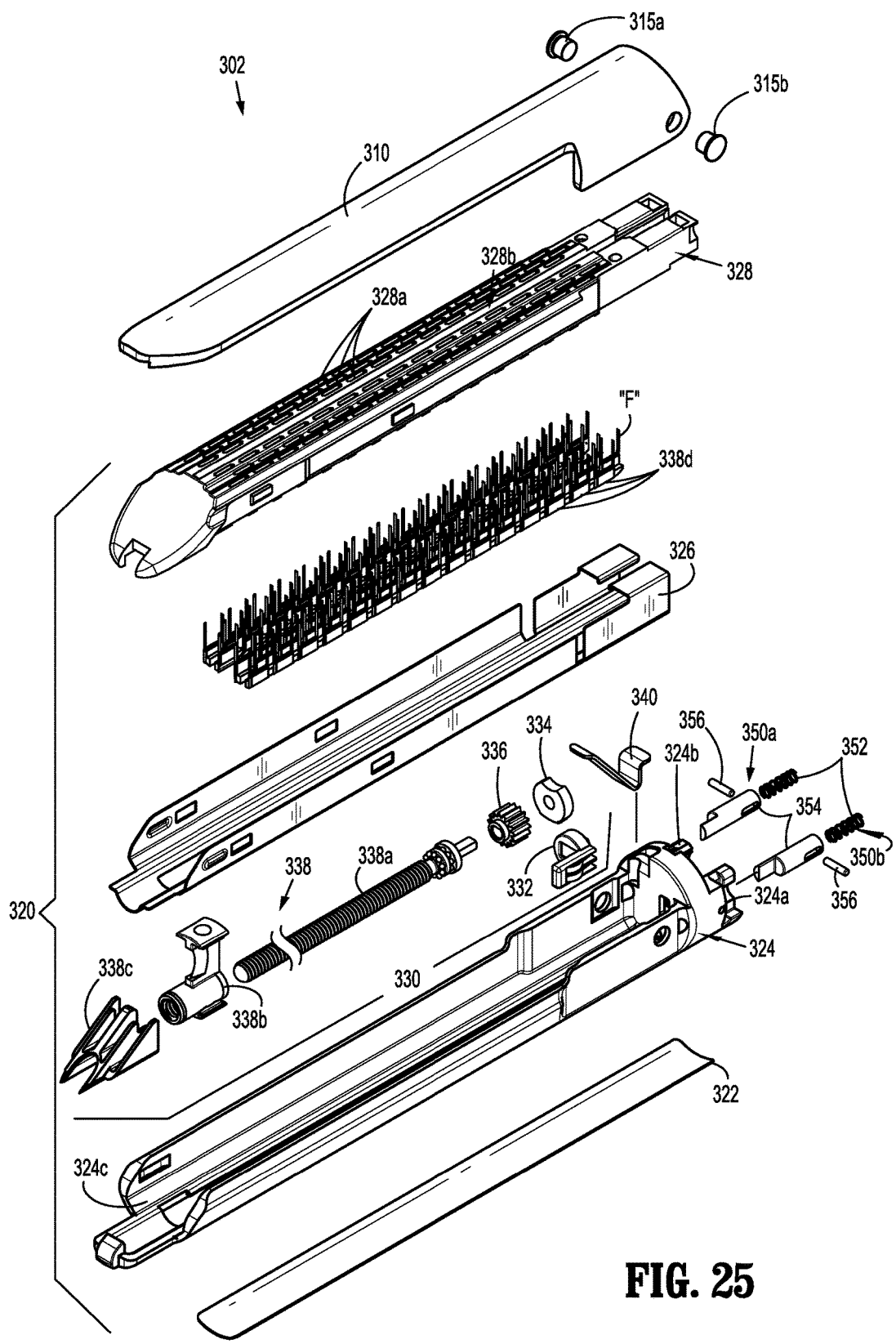
FIG. 25 is a perspective view, with parts separated, of an exemplary end effector of the exemplary loading unit shown in FIG. 1.

Turning now to FIG. 25, an exemplary end effector 302 includes anvil 310 and cartridge assembly 320 that are pinned together by a pair of pins 315a, 315b and movable between open and closed conditions. Anvil 310 and cartridge assembly 320 cooperate to apply a plurality of linear rows of fasteners "F" (e.g., staples). In certain embodiments, the fasteners are of various sizes, and, in certain embodiments, the fasteners have various lengths or rows (e.g., about 30, 45 and 60 mm in length).

Cartridge assembly 320 includes a base 322 secured to a mounting portion 324, a frame portion 326, and a cartridge portion 328 defining a plurality of fastener retaining slots 328a and a knife slot 328b in a tissue engaging surface thereof. Mounting portion 324 has mating surfaces 324a, 324b on a proximal end thereof and defines a receiving channel 324c therein that supports frame portion 326, cartridge portion 328, and a fastener firing assembly 330 therein. Cartridge assembly 320 supports a biasing member 340 that engages anvil 310.

Fastener firing assembly 330 includes an electrical contact member 332 in electrical communication with handle assembly 100 (FIG. 1), a bearing member 334, a gear member 336, and a screw assembly 338. Screw assembly 338 includes a lead screw 338a, a drive beam 338b, and an actuation sled 338c that is engagable with a plurality of pusher members 338d.

Cartridge assembly 320 also supports a pair of plunger assemblies 350a, 350b. Each of the pair of plunger assemblies 350a, 350b includes a spring 352, a plunger 354, and a pin 356 that secures each plunger assembly to mounting portion 324. Plunger assemblies 350a, 350b cooperate with the proximal end of cartridge portion 328 to facilitate securement of cartridge portion 328 within mounting portion 324.

As seen in FIGS. 26A and 26B, adapter assembly 200 can include a distal coupling member 200e having a distal gear 200g and secured to a distal end of outer tube 200c. Coupling member 200e and distal gear 200g enable end effector 302 to be secured to the distal end of outer tube 200c.

For a more detailed description of similar end effectors, coupling members, and components thereof that can be used with, or adapted for use with, the presently described electromechanical surgical system 10, reference can be made to U.S. patent application Ser. No. 14/257,063, filed on Apr. 21, 2014, the entire contents of which are incorporated by reference herein as noted above.

Referring again to FIGS. 1-25, once the components of electromechanical surgical system 10 are coupled together, one or more of actuators 104a-104c of handle assembly 100 can be manipulated to enable drive assembly 110 of handle assembly 100 to operate loading unit 300 (and/or end effector 302).

Selector motor 128 is actuatable to rotate selector cam 128 between a first position or firing state, a second position or rotation state, and a third position or articulation state. In each of the firing, rotation, and articulation states, one of the first, second, and third output assemblies 130a, 130b, 130c is received within recess 126d of selector cam 126 and disposed in an engaged position (e.g., extended) while the other two output assemblies of the first, second, and third output assemblies 130a, 130b, 130c are separated from recess 126d of selector cam 126 and disposed in a disengaged position (e.g., compressed).

In the engaged position, engagement key 136 of one respective output assembly of first, second, and third output assemblies 130a, 130b, 130c is extended from output shaft 132 of the respective output assembly so that flanges 136d, 136c of the respective engagement key 136 are positioned between inner teeth 138b of output gear 138 of the respective output assembly and in coupling region 133 of output shaft 132 of the respective output assembly 130a.

In the disengaged position, rounded tips 136a of engagement keys 136 of two of the output assemblies of first, second, and third output assemblies 130a, 130b, 130c are in contact with, and compressed against, the compression surface 126f of selector cam 126 such that flanges 136d, 136c of the two respective output assemblies are longitudinally offset from, and distal to, inner teeth 138b of output gears 138 of the two respective output assemblies.

With teeth 138a of output gear 138 of first output assembly 130a simultaneously enmeshed with teeth 122c of drive gear 122c, and teeth 138a of output gears 138 of respective second and third output assemblies 130b, 130c; rotation of drive gear 122c rotates all output gears 138 of first, second, and third output assemblies 130a, 130b, 130c. However, only in the engaged position, can the respective output assembly drive the respective driver head 132i of the respective output assembly.

To change between the firing, rotation, and articulation states, activation of selector motor 128 rotates selector cam 128 around drive motor assembly 122 such that the one output assembly 130a, 130b, or 130c, in the engaged position, moves to the disengaged position while one of the two disengaged output assemblies 130a, 130b, and/or 130c moves to the engaged position and the other of the two disengaged output assemblies 130a, 130b, and/or 130c moves from a first disengaged position to a second disengaged position. Movement between the engaged and disengaged positions (e.g., one of the output assemblies 130a, 130b, or 130c moves from a disengaged position into an engaged position, and another one of the output assemblies 130a, 130b, or 130c moves from the engaged position into a disengaged position) causes rounded tips 136a of respective engagement keys 136 to cam along tapered surfaces 126e of recess 126d of selector cam 126. Movement of one of the output assemblies from the first disengaged position to the second disengaged position causes rounded tip 136a of one of the first, second, and third output assemblies 130a, 130b, 130c to cam along compression surface 126f of selector cam 126 while maintaining the respective output assembly in a compressed state.

With respect to the firing state of selector cam 126, first output assembly 130a is disposed in the engaged position while second and third assemblies 130b, 130c are disposed in the disengaged position such that actuator 104a can be actuated to fire loading unit 300 (and/or end effector 302). More specifically, depression of actuator 104a causes motor 122a to rotate drive gear 122c. If selector cam 126 is in one of the rotation or articulation states before depressing actuator 104a, circuit boards 118a, 118b of handle assembly 100 communicate with selector motor 128 to rotate selector cam 126 into the firing state, as described above, before actuating motor 122a to rotate drive gear 122c. Once selector cam 126 is in the firing state, as drive gear 122c of drive motor assembly 122 rotates, output gear 138 of first output assembly 130a rotates driver head 132i of first output assembly 130a while output gears 138 of second and third output assemblies 130b, 130c rotate around their respective output shafts 132 such that driver heads 132i of second and third output assemblies 130b, 130c do not rotate. Rotation of driver head 132i of first output assembly 130a rotates first input coupler 210a of adapter assembly 200 to rotate firing shaft 214. Rotation of firing shaft 214 causes lead screw 338a of end effector 302 to rotate and advance drive beam 338b and actuation sled 338c distally along anvil and cartridge assemblies 310, 320 to fire fasteners "F."

With respect to the rotation state of selector cam 126, second output assembly 130b is disposed in the engaged position while first and third output assemblies 130a, 130c are disposed in the disengaged position such that actuator 104c can be rotated to rotate loading unit 300 (and/or end effector 302) about longitudinal axis "L" relative to handle assembly 100. More specifically, rotation of actuator 104c causes motor 122a to rotate drive gear 122c. If selector cam 126 is in one of the firing or articulation states before rotation of actuator 104c, circuit boards 118a, 118b of handle assembly 100 communicate with selector motor 128 to rotate selector cam 126 into the rotation state, as described above, before actuating motor 122a to rotate drive gear 122c. Once selector cam 126 is in the rotation state, as drive gear 122c of drive motor assembly 120 rotates, output gear 138 of second output assembly 130b rotates driver head 132i of second output assembly 130a while output gears 138 of first and third output assemblies 130a, 130c rotate around their respective output shafts 132 such that driver heads 132i of second and third output assemblies 130b, 130c do not rotate. Rotation of driver head 132i of second output assembly 130b rotates second input coupler 210b of adapter assembly 200 to rotate rotation shaft 218. As rotation shaft 218 rotates, rotation gear 218a of rotation shaft 218 turns rotation ring gear 220 and rotates distal housing 200b and outer tube 200c of adapter assembly 200. Rotation of outer tube 200c causes loading unit 300 (and/or end effector 302) to rotate about longitudinal axis "L."

With respect to the articulation state of selector cam 126, third output assembly 130c is disposed in the engaged position while first and second output assemblies 130a, 130b are disposed in the disengaged position such that actuator 104a can be moved laterally (e.g., left or right) relative to handle assembly 100 to articulate loading unit 300 (and/or end effector 302) relative to longitudinal axis "L" and relative to handle and adapter assemblies 100, 200. More specifically, lateral movement of actuator 104a relative to handle assembly 100 causes motor 122a to rotate drive gear 122c. If selector cam 126 is in one of the rotation or firing states before laterally moving actuator 104a, circuit boards 118a, 118b of handle assembly 100 communicate with selector motor 128 to rotate selector cam 126 into the articulation state, as described above, before actuating motor 122a to rotate drive gear 122c. Once selector cam 126 is in the articulation state, as drive gear 122c of drive motor assembly 120 rotates, output gear 138 of third output assembly 130c rotates driver head 132i of third output assembly 130c while output gears 138 of first and second output assemblies 130a, 130b rotate around their respective output shafts 132 such that driver heads 132i of first and second output assemblies 130a, 130b do not rotate. Rotation of driver head 132i of third output assembly 130c rotates third input coupler 210c of adapter assembly 200 to rotate articulation shaft 226. As articulation shaft 226 rotates, articulation sleeve 228 axially slides along longitudinal axis "L" to axially move inner tube 200d relative to outer tube 200c and cause loading unit 300 (and/or end effector 302) to articulate relative to adapter assembly 200 and longitudinal axis "L."

Any of the components described herein may be fabricated from either metals, plastics, resins, composites or the like taking into consideration strength, durability, wearability, weight, resistance to corrosion, ease of manufacturing, cost of manufacturing, and the like.

It is also contemplated that any of the rotatable components described herein can be rotated in clockwise and/or counterclockwise directions about their respective longitudinal axes.

In embodiments, any of the components described herein, such as the loading unit and/or adapter, can include one or more microchips, such as, for example a one-wire microchip (e.g., microchip model nos. DS2465, DS28E15, and/or DS2432, available from MAXIM INTEGRATED™, San Jose, Calif.) that electrically couple to the circuit board/controller of handle assembly 100. Exemplary one-wire microchips are shown and described in U.S. Pat. No. 6,239, 732, the entire contents of which are incorporated by reference herein. Any of these chips can include encrypted authentication (e.g., SULU ID) and/or may be one wire compatible.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An electromechanical surgical system comprising:
a handle assembly;
a drive motor supported in the handle assembly and extending to a drive gear;
a selector cam defining a recess;
a selector motor extending to a selector gear, the selector gear positioned to move the selector cam between a first position and a second position;
a first output assembly including a first output shaft and a first output gear, the first output shaft selectively coupled to the first output gear by a first engagement key, the first output gear rotatable with the drive gear of the drive motor, the first engagement key positionable within the recess of the selector cam while the selector cam is in the first position to engage the first output gear with the first output shaft, the first output shaft rotatable with the first output gear in response to rotation of the drive gear of the drive motor while the first output gear is coupled to the first output shaft, the first output gear being rotatable relative to the first output shaft while the selector cam is in the second position; and
a second output assembly including a second output shaft and a second output gear, the second output shaft selectively coupled to the second output gear by a second engagement key, the second output gear engaged with the first output gear of the first output assembly, the second engagement key positionable within the recess of the selector cam while the selector cam is in the second position to engage the second output gear with the second output shaft, the second output shaft rotatable with the second output gear in response to rotation of the drive gear of the drive motor while the second output gear is coupled to the second output shaft, the second output gear being rotatable relative to the second output shaft while the selector cam is in the first position.

2. The electromechanical surgical system of claim 1, wherein the first engagement key and the first output shaft are coupled by a first spring, the first spring positioned to bias the first engagement key toward the selector cam.

3. The electromechanical surgical system of claim 2, wherein the selector cam includes a compression surface adjacent to the recess of the selector cam, the compression surface positioned to urge the first engagement key toward the first output shaft and exert compression forces on the first spring while the first engagement key is in contact with the compression surface of the selector cam.

4. The electromechanical surgical system of claim 1, wherein the first engagement key includes a flange extending therefrom and the first output gear includes inner teeth, wherein the flange of the first engagement key is slidable through a slot defined in the first output shaft between a disengaged position and an engaged position to selectively engage the first output gear with the first output shaft, and wherein in the engaged position, the flange of the first engagement key is engaged with the inner teeth of the first output gear and the slot of the first output shaft so that the first output shaft rotates with the first output shaft.

5. The electromechanical surgical system of claim 4, wherein in the disengaged position, the flange of the first engagement key is engaged with the slot of the first output shaft and spaced from the first output gear such that the first output gear rotates relative to the first output shaft.

6. The electromechanical surgical system of claim 1, wherein the recess of the selector cam includes tapered sidewalls and the first engagement key includes a rounded tip, and wherein the rounded tip is configured to cam along the tapered sidewalls of the recess as the selector cam moves between the first and second positions.

7. The electromechanical surgical system of claim 1, wherein the second engagement key and the second output shaft are coupled by a second spring, the second spring positioned to bias the second engagement key toward the selector cam.

8. The electromechanical surgical system of claim 7, wherein the selector cam includes a compression surface adjacent to the recess of the selector cam, the compression surface positioned to urge the second engagement key toward the second output shaft and exert compression forces on the second spring while the second engagement key is in contact with the compression surface of the selector cam.

9. The electromechanical surgical system of claim 1, wherein the second engagement key includes a flange extending therefrom and the second output gear includes inner teeth, wherein the flange of the second engagement key is slidable through a slot defined in the second output shaft between a disengaged position and an engaged position to selectively engage the second output gear with the second output shaft, and wherein in the engaged position, the flange of the second engagement key is engaged with the inner teeth of the second output gear and the slot of the second output shaft so that the second output shaft rotates with the second output shaft.

10. The electromechanical surgical system of claim 9, wherein in the disengaged position, the flange of the second engagement key is engaged with the slot of the second output shaft and spaced from the second output gear such that the second output gear rotates relative to the second output shaft.

11. The electromechanical surgical system of claim 1, wherein the recess includes tapered sidewalls and the second engagement key includes a rounded tip, and wherein the rounded tip is configured to cam along the tapered sidewalls of the recess of the selector cam as the selector cam moves between the first and second positions.

12. The electromechanical surgical system of claim 1, further including a third output assembly including a third output shaft and a third output gear, the third output shaft selectively coupled to the third output gear by a third engagement key, the third output gear engaged with the first output gear of the first output assembly, the third engagement key positionable within the recess of the selector cam while the selector cam is in a third position to engage the third output gear with the third output shaft, the third output shaft rotatable with the third output gear in response to rotation of the drive gear of the drive motor while the third output gear is engaged with the third output shaft, the third output gear being rotatable relative to the third output shaft while the selector cam in is in the first and second positions.

13. The electromechanical surgical system of claim 12, wherein the third engagement key and the third output shaft are coupled by a third spring, the third spring positioned to bias the third engagement key toward the selector cam.

14. The electromechanical surgical system of claim 13, wherein the selector cam includes a compression surface adjacent to the recess of the selector cam, the compression surface positioned to urge the third engagement key toward the third output shaft and exert compression forces on the third spring while the third engagement key is in contact with the compression surface of the selector cam.

15. The electromechanical surgical system of claim 12, wherein the third engagement key includes a flange extending therefrom and the third output gear includes inner teeth, wherein the flange of the third engagement key is slidable through a slot defined in the third output shaft between a disengaged position and an engaged position to selectively engage the third output gear with the third output shaft, and wherein in the engaged position, the flange of the third engagement key is engaged with the inner teeth of the third output gear and the slot of the third output shaft such that the third output gear and the third output shaft move together.

16. The electromechanical surgical system of claim 15, wherein in the disengaged position, the flange of the third engagement key is engaged with the slot of the third output shaft and spaced from the third output gear so that the third output gear rotates relative to the third output shaft.

17. An electromechanical surgical system, comprising:
an adapter assembly having proximal and distal ends;
a loading unit removably coupled to the distal end of the adapter assembly;
a handle assembly coupled to the proximal end of the adapter assembly, the handle assembly including:
a drive motor;
a drive gear coupled to the drive motor;
a selector cam defining a recess;
a selector motor extending to a selector gear, the selector gear positioned to move the selector cam between a first position and a second position;
a first output assembly including a first output shaft and a first output gear, the first output gear rotatable with the drive gear of the drive motor, the first output shaft rotatable with the first output gear while the selector cam is in the first position; and
a second output assembly including a second output shaft and a second output gear, the second output gear engaged with the first output gear of the first output assembly, the second output shaft rotatable with the second output gear while the selector cam is in the second position.

18. The electromechanical surgical system of claim 17, wherein at least one of the first and second output shafts is selectively coupled to a respective one of the first and second output gears by an engagement key.

19. The electromechanical surgical system of claim 17, wherein the adapter assembly is removably coupled to the handle assembly by at least one of: a spring loaded button or a spring loaded ejector pin.

20. An electromechanical surgical system, comprising:
an adapter assembly having proximal and distal ends, the proximal end including first and second input couplers;
a loading unit removably coupled to the distal end of the adapter assembly and operably coupled to the first and second input couplers of the adapter assembly; and
a handle assembly coupled to the proximal end of the adapter assembly, the handle assembly including:
a drive motor;
a drive gear coupled to the drive motor;
a selector cam defining a recess;
a selector motor extending to a selector gear, the selector gear positioned to move the selector cam between a first position and a second position;
a first output gear rotatable with the drive gear of the drive motor;
a first output shaft rotatable with the first output gear and coupled to the first input coupler of the adapter assembly to drive the first input coupler while the selector cam is in the first position;
a second output gear engaged with the first output gear; and
a second output shaft rotatable with the second output gear and coupled to the second input coupler of the adapter assembly to drive the second input coupler while the selector cam is in the second position.

* * * * *